United States Patent
Nakahara et al.

(10) Patent No.: US 9,304,393 B2
(45) Date of Patent: Apr. 5, 2016

(54) RADIATION-SENSITIVE RESIN COMPOSITION AND COMPOUND

(71) Applicant: JSR CORPORATION, Tokyo (JP)

(72) Inventors: Kazuo Nakahara, Tokyo (JP); Ken Maruyama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 98 days.

(21) Appl. No.: 13/929,357

(22) Filed: Jun. 27, 2013

(65) Prior Publication Data

US 2013/0288179 A1   Oct. 31, 2013

Related U.S. Application Data

(63) Continuation of application No. PCT/JP2011/080118, filed on Dec. 26, 2011.

(30) Foreign Application Priority Data

Dec. 28, 2010   (JP) .................................. 2010-293362

(51) Int. Cl.

| | |
|---|---|
| *G03F 7/004* | (2006.01) |
| *C07C 309/06* | (2006.01) |
| *C07C 309/07* | (2006.01) |
| *C07C 309/12* | (2006.01) |
| *C07C 309/19* | (2006.01) |
| *C07C 22/02* | (2006.01) |
| *C07C 381/12* | (2006.01) |
| *C07D 307/77* | (2006.01) |
| *C08K 5/07* | (2006.01) |
| *C07C 22/08* | (2006.01) |
| *C07C 25/18* | (2006.01) |
| *G03F 7/039* | (2006.01) |
| *G03F 7/11* | (2006.01) |
| *G03F 7/20* | (2006.01) |

(52) U.S. Cl.
CPC ............... *G03F 7/004* (2013.01); *C07C 22/02* (2013.01); *C07C 22/08* (2013.01); *C07C 25/18* (2013.01); *C07C 309/19* (2013.01); *C07C 381/12* (2013.01); *C07D 307/77* (2013.01); *C08K 5/07* (2013.01); *G03F 7/0045* (2013.01); *G03F 7/0046* (2013.01); *G03F 7/0392* (2013.01); *G03F 7/0397* (2013.01); *G03F 7/11* (2013.01); *G03F 7/2041* (2013.01); *C07C 2101/08* (2013.01); *C07C 2101/14* (2013.01); *C07C 2101/16* (2013.01); *C07C 2102/42* (2013.01)

(58) Field of Classification Search
CPC .. C07C 309/02; C07C 309/03; C07C 309/04; C07C 309/06; C07C 309/07; C07C 309/12; C07C 309/17; C07C 309/19; G03F 7/004; G03F 7/039; G03F 7/0392; G03F 7/0395
See application file for complete search history.

(56) References Cited

U.S. PATENT DOCUMENTS

| | | | |
|---|---|---|---|
| 4,491,628 A | 1/1985 | Ito et al. | |
| 2004/0242724 A1* | 12/2004 | Saito | ............................. 523/125 |
| 2005/0186505 A1* | 8/2005 | Kodama et al. | ............ 430/270.1 |

(Continued)

FOREIGN PATENT DOCUMENTS

| | | |
|---|---|---|
| JP | 51-112865 | 10/1976 |
| JP | 59-045439 | 3/1984 |

(Continued)

OTHER PUBLICATIONS

Machine translation of JP 2000-327654, published on Nov. 28, 2000.*
Machine translation of JP 2007-246835, published on Sep. 27, 2007.*
Machine translation of JP 2003-327572, published on Nov. 19, 2003.*
Office Action issued Oct. 7, 2014 in Japanese Patent Application No. 2012-550948 (with English language translation).

(Continued)

*Primary Examiner* — Anca Eoff
(74) *Attorney, Agent, or Firm* — Oblon, McClelland, Maier & Neustadt, L.L.P.

(57) ABSTRACT

A radiation-sensitive resin composition includes a compound represented by a formula (1), and a polymer that includes a structural unit having an acid-labile group. $R^1$ and $R^4$ each independently represent a hydrogen atom, or the like. $R^2$ and $R^3$ each independently represent a hydrogen atom or the like. $X^1$ and $X^2$ each independently represent a hydrogen atom, or the like, or $X^1$ and $X^2$ taken together represent —S—, —O—, —SO$_2$—, or the like. A represents an ethanediyl group, wherein at least one hydrogen atom included in $X^1$, $X^2$ and A is substituted by —Y—SO$_3^-$M$^+$. Y represents an alkanediyl group having 1 to 10 carbon atoms, or the like. M$^+$ represents a monovalent onium cation. In the case where —Y—SO$_3^-$M$^+$ is present in a plurality of number, a plurality of Ys are each identical or different and a plurality of M$^+$s are each identical or different.

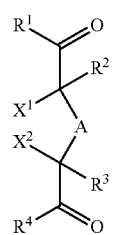

(1)

11 Claims, No Drawings

(56) References Cited

U.S. PATENT DOCUMENTS

2012/0164582 A1* 6/2012 Maruyama ................ 430/285.1
2013/0280658 A1* 10/2013 Maruyama ................ 430/285.1

FOREIGN PATENT DOCUMENTS

| | | | |
|---|---|---|---|
| JP | 2000-327654 | * | 11/2000 |
| JP | 2002-255877 | | 9/2002 |
| JP | 2003-327572 | * | 11/2003 |
| JP | 2004-317907 | | 11/2004 |
| JP | 2005-126598 | | 5/2005 |
| JP | 2006-227632 | | 8/2006 |
| JP | 2007-246835 | * | 9/2007 |
| WO | WO 2005/069076 | | 7/2005 |
| WO | WO 2005/101129 | | 10/2005 |
| WO | WO 2006/035790 | | 4/2006 |
| WO | WO 2007/116664 | | 10/2007 |

OTHER PUBLICATIONS

International Search Report for corresponding International Application No. PCT/JP2011/080118, Jan. 31, 2012.

* cited by examiner

RADIATION-SENSITIVE RESIN COMPOSITION AND COMPOUND

CROSS-REFERENCE TO RELATED APPLICATIONS

The present application is a continuation application of International Application No. PCT/JP2011/080118, filed Dec. 26, 2011, which claims priority to Japanese Patent Application No. 2010-293362, filed Dec. 28, 2010. The contents of these applications are incorporated herein by reference in their entirety.

BACKGROUND OF THE INVENTION

1. Field of the Invention

The present invention relates to a radiation-sensitive resin composition, and a compound.

2. Discussion of the Background

At present, a resist pattern having a line width of about 90 nm can be formed using an ArF excimer laser. Along with miniaturization of structures in various types of electronic devices such as semiconductor devices and liquid crystal devices, formation of even finer patterns in lithography steps would be hereafter demanded.

Conventionally, a chemically amplified type resist composition has been extensively employed in such pattern formation. The chemically amplified type resist composition contains an acid generating component that generates an acid upon exposure, and a resin component whose solubility in developer solutions varies by the action of this acid (see Japanese Unexamined Patent Application, Publication No. S59-45439), whereby a pattern can be formed using the difference of rates of dissolution between a light-exposed site and a light-unexposed site. When more accurate control of the line width should be carried out, the chemically amplified resist composition is required to have not only general characteristics such as resolving performances and sensitivity, but also characteristics for accurate control of fine shapes such as MEEF (Mask Error Enhancement Factor) performances that serve as a marker that is an indicative of mask reproducibility, and the like.

In order to control fine shapes in this manner, a technique in which a basic compound is added to a conventional resist composition to prevent diffusion of the acid generated from an acid generating agent has been known. In addition, a number of acid generating agents have been developed so far, and for example, a radiation-sensitive acid generating agent having a trifluoromethanesulfonyl structure, a radiation-sensitive acid generating agent having a sulfonyl structure provided by binding to a large organic group such as a 10-camphorsulfonyl structure, and the like have been known. However, further improvement of MEEF performances, the resultant pattern configuration, and the like of the radiation-sensitive compositions including these is needed.

SUMMARY OF THE INVENTION

According to one aspect of the present invention, a radiation-sensitive resin composition includes a compound represented by a formula (1), and a polymer that includes a structural unit having an acid-labile group.

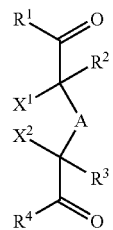

(1)

In the formula (1), $R^1$ and $R^4$ each independently represent a hydrogen atom, a hydroxyl group or a monovalent organic group; $R^2$ and $R^3$ each independently represent a hydrogen atom or a monovalent organic group; $X^1$ and $X^2$ each independently represent a hydrogen atom, a hydroxyl group, a thiol group, a sulfonyl group or a monovalent organic group, or $X^1$ and $X^2$ taken together represent —S—, —O—, —SO$_2$—, an alkanediyl group having 1 to 10 carbon atoms or a combined group thereof; and A represents an ethanediyl group, wherein at least one hydrogen atom included in $X^1$, $X^2$ and A is substituted by —Y—SO$_3^-$M$^+$, wherein Y represents an alkanediyl group having 1 to 10 carbon atoms that is not substituted or substituted with a fluorine atom, and M$^+$ represents a monovalent onium cation, and in the case where —Y—SO$_3^-$M$^+$ is present in a plurality of number, a plurality of Ys are each identical or different and a plurality of M$^+$s are each identical or different.

According to another aspect of the present invention, a compound is represented by a formula (1).

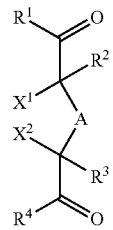

(1)

In the formula (1), $R^1$ and $R^4$ each independently represent a hydrogen atom, a hydroxyl group or a monovalent organic group; $R^2$ and $R^3$ each independently represent a hydrogen atom or a monovalent organic group; $X^1$ and $X^2$ each independently represent a hydrogen atom, a hydroxyl group, a thiol group, a sulfonyl group or a monovalent organic group, or $X^1$ and $X^2$ taken together represent —S—, —O—, —SO$_2$—, an alkanediyl group having 1 to 10 carbon atoms or a combined group thereof; and A represents an ethanediyl group, wherein at least one hydrogen atom included in $X^1$, $X^2$ and A is substituted by —Y—SO$_3^-$M$^+$, wherein Y represents an alkanediyl group having 1 to 10 carbon atoms that is not substituted or substituted with a fluorine atom, and M$^+$ represents a monovalent onium cation, and in the case where —Y—SO$_3^-$M$^+$ is present in a plurality of number, a plurality of Ys are each identical or different and a plurality of M$^+$s are each identical or different.

According to further aspect of the present invention, a compound is represented by a formula (3). The compound is for use in synthesis of the compound according to claim 5.

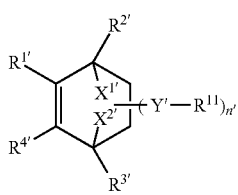

(3)

In the formula (3), $R^{1'}$ and $R^{4'}$ each independently represent a hydrogen atom, a hydroxyl group or a monovalent organic group; $R^{2'}$ and $R^{3'}$ each independently represent a hydrogen atom or a monovalent organic group; $R^{11}$ represents a bromine atom, a chlorine atom or an iodine atom; $X^{1'}$ and $X^{2'}$ each independently represent a hydrogen atom, a hydroxyl group, a thiol group, a sulfonyl group or a monovalent organic group, or $X^{1'}$ and $X^{2'}$ taken together represent —S—, —O—, —SO$_2$—, an alkanediyl group having 1 to 10 carbon atoms or a combined group thereof; Y' represents an alkanediyl group having 1 to 10 carbon atoms that is not substituted or substituted with a fluorine atom; and n' is an integer of 1 to 4, wherein in the case where n' is 2 or greater, a plurality of Y's are each identical or different and a plurality of $R^{11}$s are each identical or different.

DESCRIPTION OF THE EMBODIMENTS

According to an embodiment of the present invention, a radiation-sensitive resin composition contains (A) a compound represented by the following formula (1) (hereinafter, may be also referred to as "compound (A)"), and (B) a polymer that includes a structural unit having an acid-labile group (hereinafter, may be also referred to as "polymer (B)").

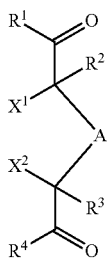

(1)

wherein, in the formula (1), $R^1$ and $R^4$ each independently represent a hydrogen atom, a hydroxyl group or a monovalent organic group; $R^2$ and $R^3$ each independently represent a hydrogen atom or a monovalent organic group; $X^1$ and $X^2$ each independently represent a hydrogen atom, a hydroxyl group, a thiol group, a sulfonyl group or a monovalent organic group, or $X^1$ and $X^2$ taken together represent —S—, —O—, —SO$_2$—, an alkanediyl group having 1 to 10 carbon atoms or a combined group thereof; and A represents an ethanediyl group, wherein at least one hydrogen atom included in $X^1$, $X^2$ and A is substituted by —Y—SO$_3^-$M$^+$, wherein Y represents an alkanediyl group having 1 to 10 carbon atoms that is not substituted or substituted with a fluorine atom, and M$^+$ represents a monovalent onium cation, and in a case where —Y—SO$_3^-$M$^+$ is present in a plurality of number, a plurality of Ys are each identical or different and a plurality of M$^+$s are each identical or different.

In the radiation-sensitive resin composition, the compound (A) suitably serves as an acid generating agent. According to the compound (A), due to having the above-specified structure having a plurality of polar groups, an affinity to the polymer (B) having an acid-labile group is increased, and thus diffusion of the acid is appropriately controlled. As a result, the radiation-sensitive composition can satisfy basic characteristics such as sensitivity and resolving ability, as well as MEEF performances enough.

The compound (A) is preferably a compound represented by the following formula (2). In the radiation-sensitive resin composition, when the compound (A) has the following specified structure that includes a cyclic structure, diffusion of the acid is more appropriately controlled, and MEEF performances are further improved.

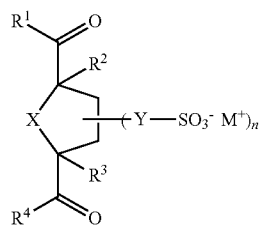

(2)

wherein, in the formula (2), $R^1$ to $R^4$, Y and M$^+$ are as defined in the above formula (1); X represents —S—, —O—, —SO$_2$—, an alkanediyl group having 1 to 10 carbon atoms or a combined group thereof; and n is an integer of 1 to 4.

It is preferred that $R^1$ represents —OR$^5$, and $R^4$ represents —OR$^6$, wherein $R^5$ and $R^6$ each independently represent an alkyl group having 1 to 10 carbon atoms, an alicyclic group having 3 to 10 carbon atoms or a group having a lactone structure having 4 to 12 carbon atoms. In the radiation-sensitive resin composition, when the compound (A) has the diester structure described above, a polarity is further increased, and the MEEF performances are further improved.

It is preferred that the polymer (B) further includes a structural unit having a lactone structure or a cyclic carbonate structure, a structural unit having a polar group, or a combination thereof. In the radiation-sensitive resin composition, when the polymer (B) further includes the structural unit having the above-specified structure, basic characteristics of a resist such as adhesiveness to a substrate of a resist film can be improved. In addition, since an affinity of the compound (A) to the polymer (B) is more enhanced according to the radiation-sensitive resin composition, the MEEF performances can be consequently improved.

The compound of the embodiment of the present invention is represented by the following formula (1):

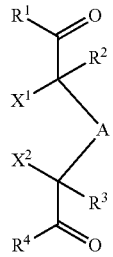

(1)

wherein, in the formula (1), $R^1$ and $R^4$ each independently represent a hydrogen atom, a hydroxyl group or a monovalent organic group; $R^2$ and $R^3$ each independently represent a hydrogen atom or a monovalent organic group; $X^1$ and $X^2$ each independently represent a hydrogen atom, a hydroxyl group, a thiol group, a sulfonyl group or a monovalent organic group, or $X^1$ and $X^2$ taken together represent —S—, —O—, —SO$_2$—, an alkanediyl group having 1 to 10 carbon atoms or a combined group thereof; and A represents an ethanediyl group, wherein at least one hydrogen atom included in $X^1$, $X^2$ and A is substituted by —Y—SO$_3^-$M$^+$, wherein Y represents an alkanediyl group having 1 to 10 carbon atoms that is not substituted or substituted with a fluorine atom, and M$^+$ represents a monovalent onium cation, and in a case where —Y—SO$_3^-$M$^+$ is present in a plurality of number, a plurality of Ys are each identical or different and a plurality of M$^+$s are each identical or different.

Due to including the above-specified structure, the compound has an appropriate polarity, and miscibility with a polymer having an acid-labile group is increased. In addition, owing to the structure that is bulky, when the compound is used as an acid generating agent of the radiation-sensitive resin composition, diffusion of the acid is appropriately controlled, and can sufficiently satisfy basic characteristics such as a resolving ability, as well as also MEEF performances enough. Thus, the compound of the embodiment of the present invention may be suitably used as, for example, an acid generating agent in the radiation-sensitive resin composition. Moreover, synthesis of the compound (A) is comparatively convenient, and superior productivity is also achieved.

It is preferred that the compound of the embodiment of the present invention is represented by the following formula (2):

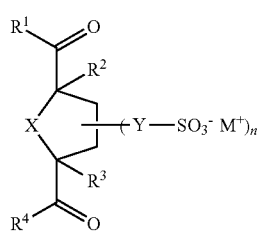

(2)

wherein, in the formula (2), $R^1$ to $R^4$, Y and M$^+$ are as defined in the above formula (1); X represents —S—, —O—, —SO$_2$—, an alkanediyl group having 1 to 10 carbon atoms or a combined group thereof; and n is an integer of 1 to 4.

When the compound has the above-specified structure that includes a cyclic structure, in a case in which the compound is used as, for example, a material of the radiation-sensitive composition, the MEEF performances of the radiation-sensitive composition can be further improved.

It is preferred that $R^1$ represents —OR$^5$, and $R^4$ represents —OR$^6$, wherein $R^5$ and $R^6$ each independently represent an alkyl group having 1 to 10 carbon atoms, an alicyclic group having 3 to 10 carbon atoms or a group having a lactone structure having 4 to 12 carbon atoms.

When the compound has the diester structure described above, a polarity is increased; therefore, in a case in which the compound is used as, for example, a material of the radiation-sensitive resin composition, the MEEF performances can be further improved.

In the embodiment of the present invention, a compound represented by the following formula (3) used in the synthesis of the compound represented by the above formula (1) may be also included.

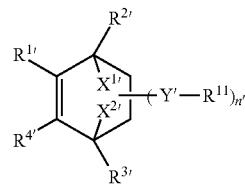

(3)

wherein, in the formula (3), $R^{1'}$ and $R^{4'}$ each independently represent a hydrogen atom, a hydroxyl group or a monovalent organic group; $R^{2'}$ and $R^{3'}$ each independently represent a hydrogen atom or a monovalent organic group; $R^{11}$ represents a bromine atom, a chlorine atom or an iodine atom; $X^{1'}$ and $X^{2'}$ each independently represent a hydrogen atom, a hydroxyl group, a thiol group, a sulfonyl group or a monovalent organic group, or $X^{1'}$ and $X^{2'}$ taken together represent —S—, —O—, —SO$_2$—, an alkanediyl group having 1 to 10 carbon atoms or a combined group thereof; Y' represents an alkanediyl group having 1 to 10 carbon atoms that is not substituted or substituted with a fluorine atom; and n' is an integer of 1 to 4, wherein in the case where n' is 2 or greater, a plurality of Y's are each identical or different and a plurality of $R^{11}$s are each identical or different.

The compound that includes the specified structure represented by the above formula (3) may be used for synthesis of, for example, the compound represented by the above formula (1) or (2) suitably used as an acid generating agent in the radiation-sensitive resin composition.

It is to be noted that as referred to herein, the term "radiation (may be referred to as 'radioactive ray')" in the "radiation-sensitive resin composition" conceptionally includes a visible light ray, a ultraviolet ray, a far ultraviolet ray, an X-ray, a charged particle ray and the like. In addition, the term "organic group" as referred to includes a group having at least one carbon atom.

According the embodiment of the present invention, a radiation-sensitive resin composition that satisfies basic characteristics such as sensitivity and resolving ability, as well as MEEF performances enough, a compound which can be suitably used as a material of the radiation-sensitive resin composition, and an intermediate compound of the synthesis thereof can be provided. The embodiments will now be described in detail.

<Radiation-Sensitive Resin Composition>

The radiation-sensitive resin composition of the embodiment of the present invention contains the compound (A) and the polymer (B). In addition, the radiation-sensitive resin composition may further contain an acid generating agent other than the compound (A), (C) a fluorine atom-containing polymer, (D) a nitrogen-containing compound, and (E) a solvent. Moreover, other optional component may be contained as long as the effects of the embodiment of the present invention are not impaired. Hereinafter, each component will be described in detail.

Compound (A)

The compound (A) contained in the radiation-sensitive resin composition is represented by the above formula (1), and serves as a radiation-sensitive acid generating agent that generates an acid upon exposure. Due to having the above-specified structure, the compound (A) is bulky and highly polar; therefore, diffusion of the acid generated upon exposure is appropriately suppressed. As a result, the radiation-sensitive resin composition containing the compound (A) is superior in MEEF performances, and formation of a favorable resist pattern is enabled. As such a compound (A), the compound represented by the above formula (2) is preferred.

In the above formula (1), $R^1$ and $R^4$ each independently represent a hydrogen atom, a hydroxyl group or a monovalent organic group; $R^2$ and $R^3$ each independently represent a hydrogen atom or a monovalent organic group; $X^1$ and $X^2$ each independently represent a hydrogen atom, a hydroxyl group, a thiol group, a sulfonyl group or a monovalent organic group, or $X^1$ and $X^2$ taken together represent —S—, —O—, —SO$_2$—, an alkanediyl group having 1 to 10 carbon atoms or a combined group thereof; and A represents an ethanediyl group, wherein at least one hydrogen atom included in $X^1$, $X^2$ and A is substituted by —Y—SO$_3^-$M$^+$, wherein Y represents an alkanediyl group having 1 to 10 carbon atoms that is not substituted or substituted with a fluorine atom, and M$^+$ represents a monovalent onium cation, and in a case where —Y—SO$_3^-$M$^+$ is present in a plurality of number, a plurality of Ys are each identical or different and a plurality of M$^+$s are each identical or different.

In the formula (2), $R^1$ to $R^4$, Y and M' are as defined in the above formula (1); X represents —S—, —O—, —SO$_2$—, an alkanediyl group having 1 to 10 carbon atoms or a combined group thereof; and n is an integer of 1 to 4.

The monovalent organic group represented by $R^1$ to $R^4$ is exemplified by an organic group such as a hydrocarbon group, a cyano group, an alkylthio group, an alkenyl group, an alkylcarbonyl group, an acyl group and a hydrocarbon group that includes a hetero atom. Examples of the hetero atom include a halogen atom, an oxygen atom, a nitrogen atom, a sulfur atom, a phosphorus atom, a silicon atom, and the like.

The monovalent organic group represented by $R^1$ and $R^4$ is preferably an alkyl group having 1 to 20 carbon atoms, an alicyclic hydrocarbon group having 3 to 20 carbon atoms, a group having a lactone structure having 4 to 20 carbon atoms, or the like, which does not include or includes —O— or —NH—. It is to be noted that "group B which includes (or does not include or includes) A" as referred to herein means both the "group B which includes (or does not include or includes) A in its skeleton chain", and "group whose a part or all of hydrogen atoms included in the B group are substituted (not substituted or substituted) by A".

Examples of the alkyl group having 1 to 20 carbon atoms include a methyl group, an ethyl group, a n-propyl group, an i-propyl group, a n-butyl group, a tert-butyl group, and the like.

Examples of the alicyclic hydrocarbon group having 3 to 20 carbon atoms include cycloalkyl groups such as a cyclobutyl group, a cyclopentyl group, a cyclohexyl group and a cyclooctyl group, a norbornyl group, a tricyclodecanyl group, a tetracyclododecanyl group, an adamantyl group, and the like.

The monovalent organic group represented by $R^1$ and $R^4$ is more preferably a group represented by —ZR$^5$ and —ZR$^6$, wherein Z represents —O— or —NH—, and $R^5$ and $R^6$ represent an alkyl group having 1 to 10 carbon atoms, an alicyclic hydrocarbon group having 3 to 10 carbon atoms or a group having a lactone structure having 4 to 12 carbon atoms.

It is preferred that Z represents —O—. $R^5$ and $R^6$ preferably represent an alkyl group having 1 to 5 carbon atoms, an alicyclic hydrocarbon group having 3 to 10 carbon atoms or a group having a lactone structure having 6 to 10 carbon atoms, and more preferably represent a methyl group, an ethyl group, a cyclohexyl group, and a norbornanelactone group.

The monovalent organic group represented by $X^1$ and $X^2$ is exemplified by an alkyl group having 1 to 10 carbon atoms which does not include or includes an oxygen atom or a sulfur atom, and the like. Examples of the alkyl group include a methyl group, an ethyl group, a propyl group, a butyl group, an octyl group, and the like.

Examples of the alkanediyl group having 1 to 10 carbon atoms taken together represented by $X^1$ and $X^2$, and the alkanediyl group having 1 to 10 carbon atoms represented by X in the above formula (2) include a methanediyl group, an ethanediyl group, a propanediyl group, a butanediyl group, a hexanediyl group, an octanediyl group, and the like.

The combined group of the above exemplified groups taken together represented by $X^1$ and $X^2$ is exemplified by groups derived by combining an alkanediyl group having 1 to 10 carbon atoms with at least one group selected from the set consisting of —S—, —O— and —SO$_2$—, and the like, and is preferably an alkanediyl group having 1 to 10 carbon atoms and including —S—, —O—, or —SO$_2$— in its skeleton chain.

The group taken together represented by $X^1$ and $X^2$, and the group represented by X in the above formula (2) are preferably —S—, —O—, —SO$_2$— or an alkanediyl group having 1 to 10 carbon atoms. Of these, an alkanediyl group having 1 to 10 carbon atoms is more preferred, and a methanediyl group and an ethanediyl group are still more preferred.

In —Y—SO$_3^-$M$^+$ included in $X^1$, $X^2$ and A as a substituent in the number of at least one, the alkanediyl group having 1 to 10 carbon atoms that is not substituted or substituted with a fluorine atom represented by Y is exemplified by groups similar to those exemplified as the alkanediyl group having 1 to 10 carbon atoms which may be taken together represented by $X^1$ and $X^2$. Among these, an ethanediyl group that is not substituted or substituted with a fluorine atom is preferred, and a perfluoroethanediyl group is more preferred.

The alkanediyl group having 1 to 10 carbon atoms represented by Y is preferably substituted with a fluorine atom, and in particular, the alkanediyl group more preferably has a fluorine atom bonding to a carbon atom adjacent to SO$_3$—. The number of —Y—SO$_3^-$M$^+$ (i.e., "n" in the above formula (2)) is preferably 1 to 4, more preferably 1 to 2, and still more preferably 1.

The monovalent onium cation represented by M$^+$ will be described later.

Specific examples of the compound represented by the above formula (1) include compounds represented by the following formulae (1-1) to (1-43), and the like.

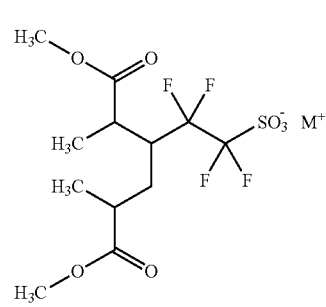

(1-1)

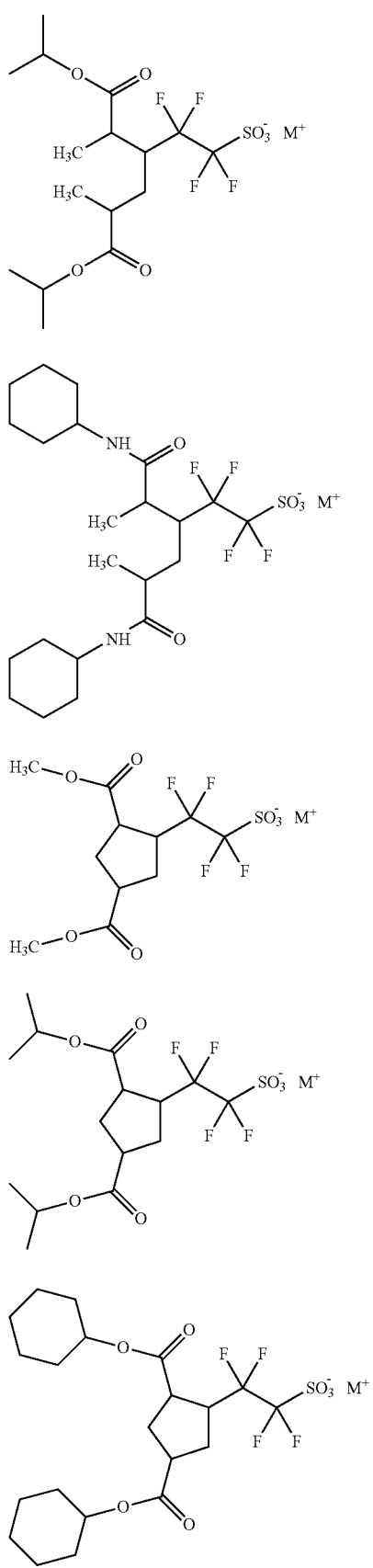
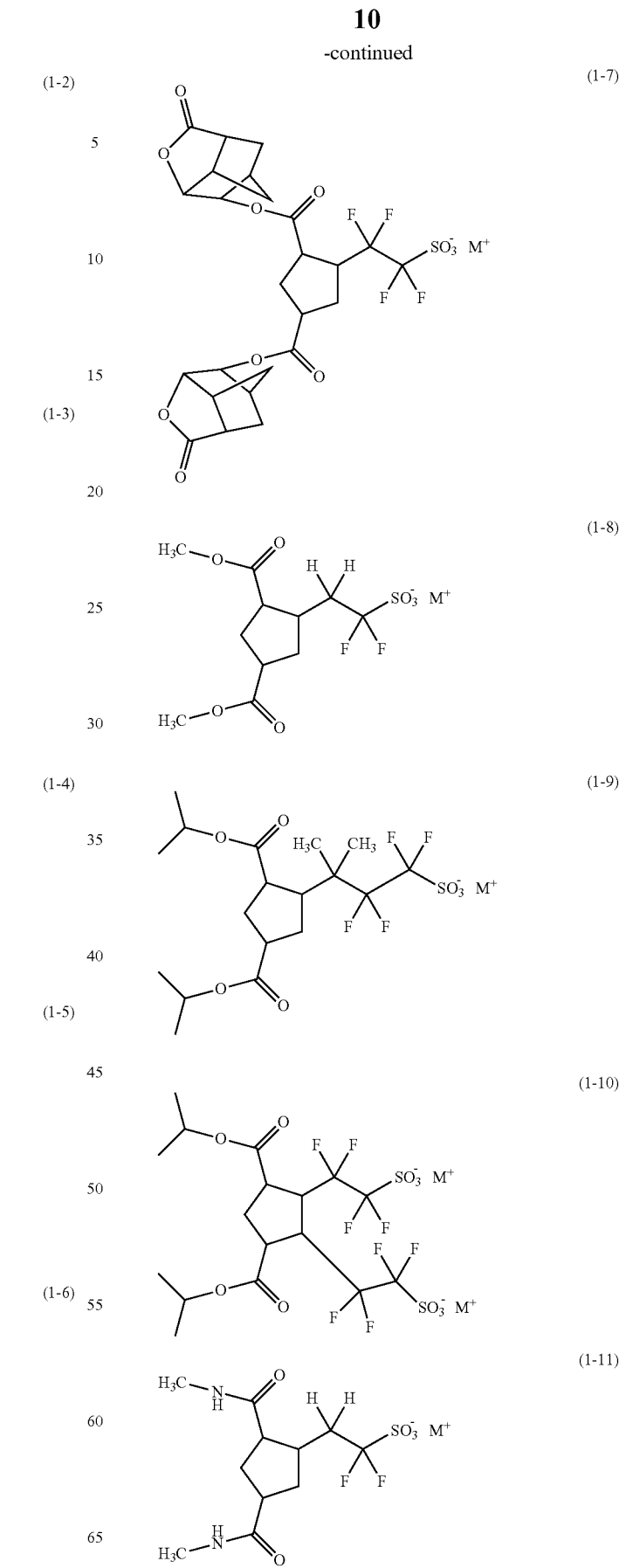

-continued
(1-12)
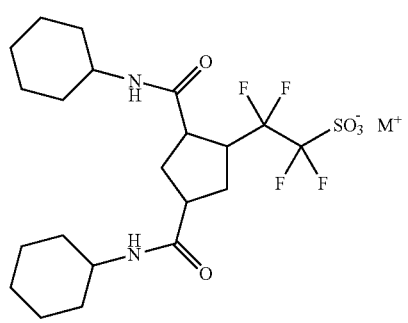
(1-13)
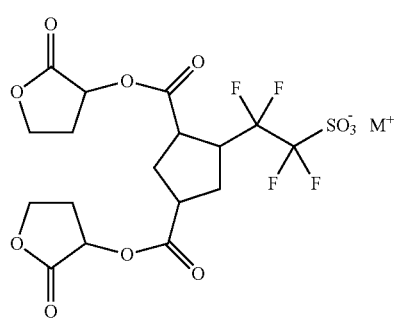
(1-14)
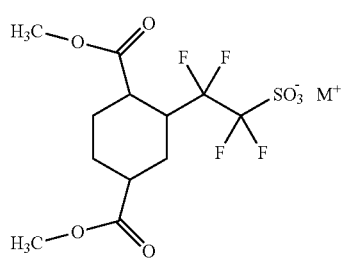
(1-15)
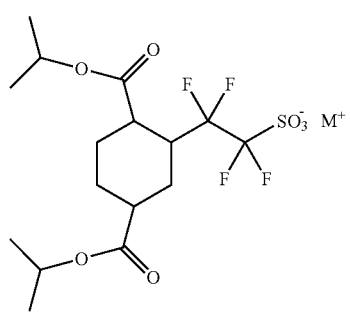
(1-16)
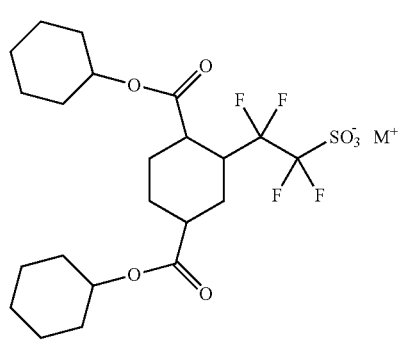
-continued
(1-17)
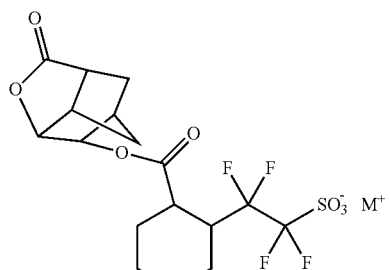
(1-18)
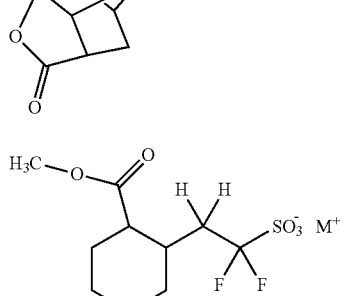
(1-19)
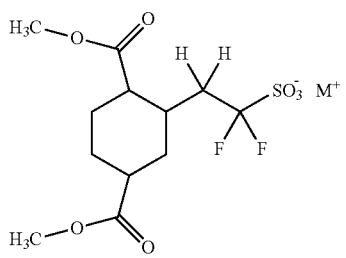
(1-20)
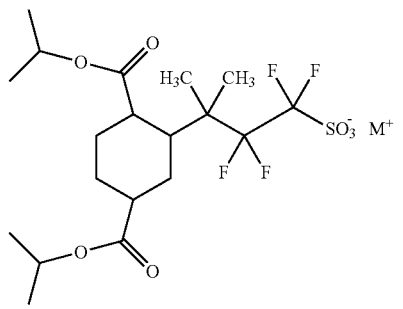
(1-21)
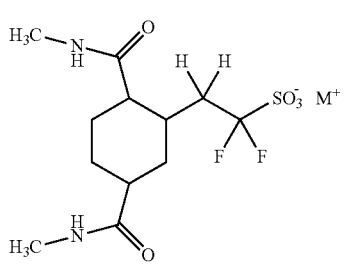

-continued
(1-22)
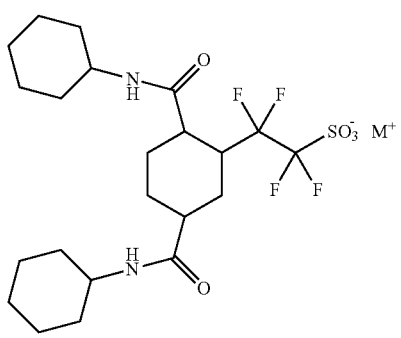
(1-23)
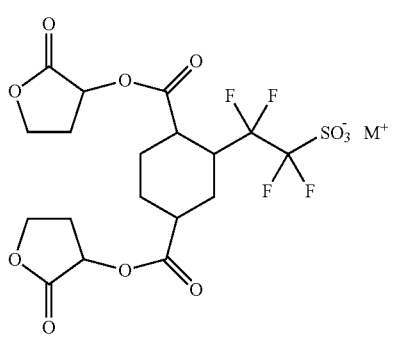
(1-24)
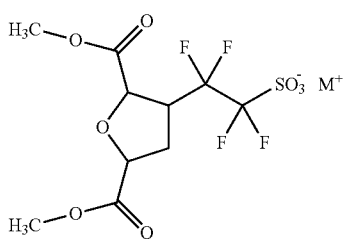
(1-25)
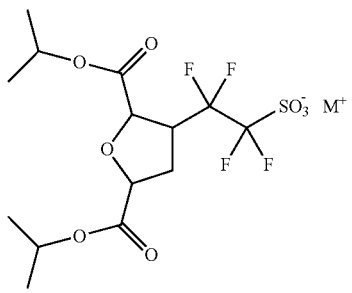
(1-26)
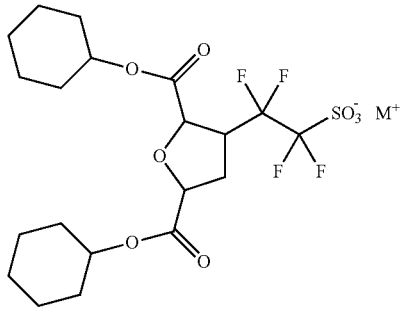
-continued
(1-27)
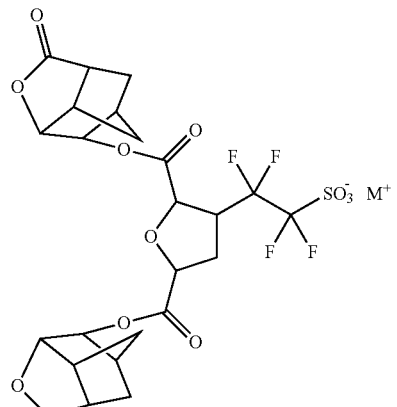
(1-28)
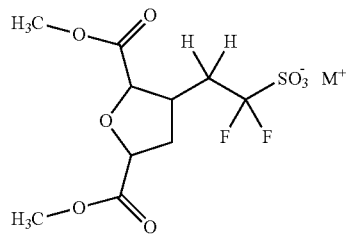
(1-29)
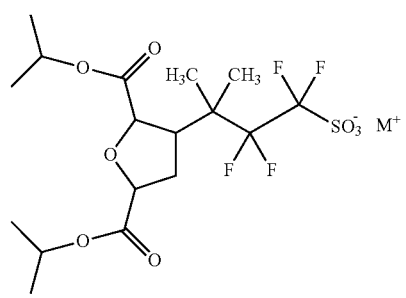
(1-30)
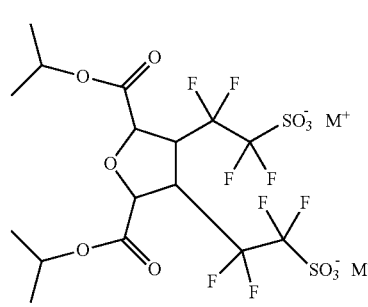
(1-31)
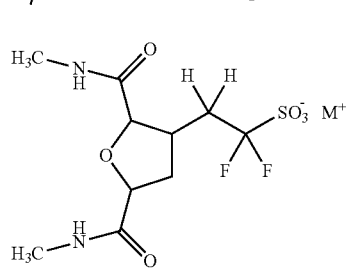

15
-continued
(1-32)
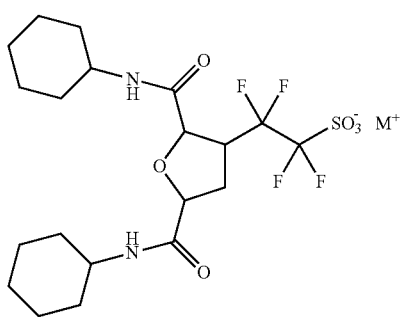
(1-33)
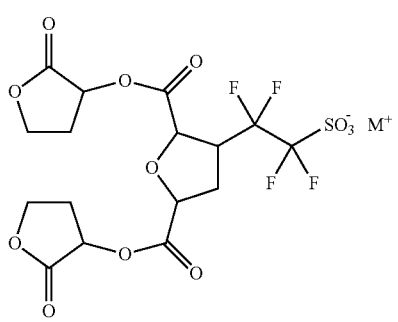
(1-34)
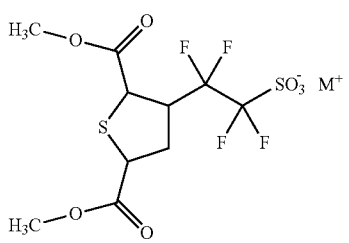
(1-35)
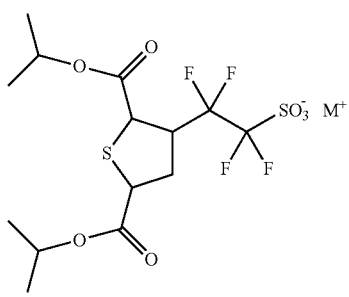
(1-36)
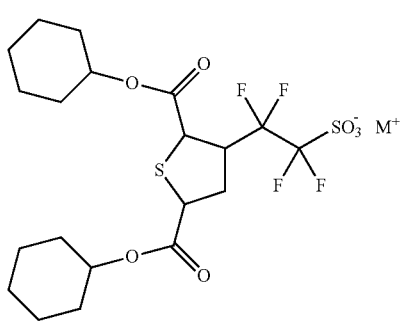
16
-continued
(1-37)
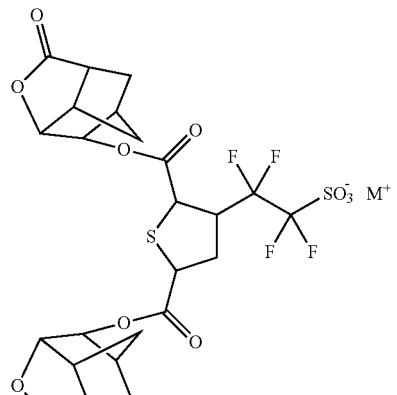
(1-38)
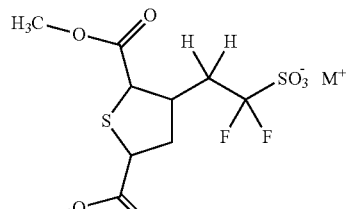
(1-39)
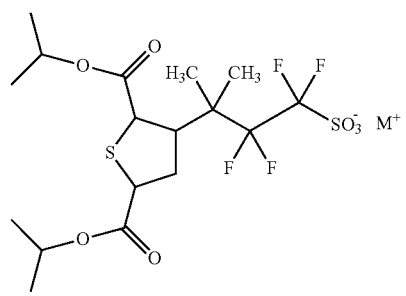
(1-40)
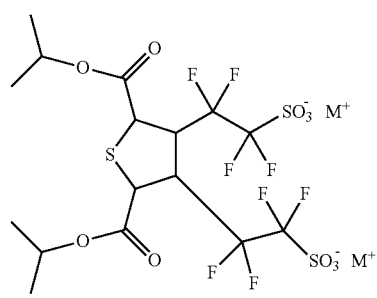
(1-41)
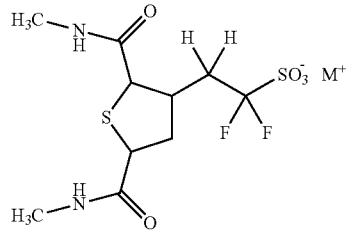

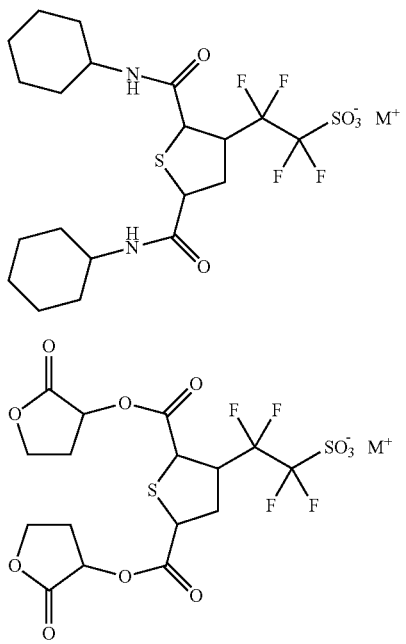

(1-42)

(1-43)

Of these, in light of improvement of MEEF performances, compounds represented by the above formulae (1-4), (1-5), (1-6), (1-7), (1-12) and (1-13) are preferred.

Examples of the monovalent onium cation represented by $M^+$ include onium cations of O, S, Se, N, P, As, Sb, Cl, Br and I. Of these, each onium cation of S and I is preferred.

Specific sulfonium cation (onium cation of S) is exemplified by a sulfonium cation represented by the following formula (4), and the like. In addition, specific iodonium cation (onium cation of I) is exemplified by an iodonium cation represented by the following formula (5), and the like.

$$R^7-\overset{R^8}{\underset{|}{S^+}}-R^9 \quad (4)$$

In the above formula (4), $R^7$, $R^8$ and $R^9$ each independently represent an alkyl group having 1 to 10 carbon atoms, or an aromatic hydrocarbon group having 6 to 18 carbon atoms. A part or all of hydrogen atoms included in the alkyl group and the aromatic hydrocarbon group are not substituted or substituted. Alternatively, any two of $R^7$, $R^8$ and $R^9$ may taken together represent a cyclic structure together with the sulfur atom to which the two of $R^7$, $R^8$ and $R^9$ each bond.

$$R^{10}-I^+-R^{11} \quad (5)$$

In the above formula (5), $R^{10}$ and $R^{11}$ each independently represent an alkyl group having 1 to 10 carbon atoms, or an aromatic hydrocarbon group having 6 to 18 carbon atoms. A part or all of hydrogen atoms included in the alkyl group and the aromatic hydrocarbon group are not substituted or substituted. Alternatively, $R^{10}$ and $R^{11}$ may taken together represent a cyclic structure together with the iodine atom to which $R^{10}$ and $R^{11}$ each bond.

Examples of the alkyl group having 1 to 10 carbon atoms represented by $R^7$ to $R^9$ in the above formula (4) include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethylhexyl group, and the like. In addition, the substituent which may be included in the alkyl group is exemplified by groups similar to those exemplified as monovalent organic groups represented by $R^2$ and $R^3$.

Examples of the aromatic hydrocarbon group having 6 to 18 carbon atoms represented by $R^7$ to $R^9$ include a phenyl group, a 1-naphthyl group, a 2-naphthyl group, a 1-anthryl group, a 1-phenanthryl group, and the like. In addition, the substituent which may be included in the aromatic hydrocarbon group is exemplified by groups similar to those exemplified as monovalent organic groups represented by $R^2$ and $R^3$.

Among the onium cations represented by the above formula (4), onium cations represented by the following formula (4-1) or (4-2) are preferred.

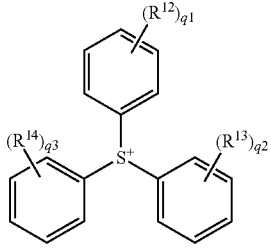

(4-1)

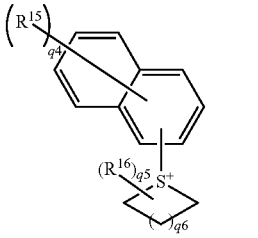

(4-2)

In the above formula (4-1), $R^{12}$ to $R^{14}$ each independently represent a hydrogen atom, an alkyl group having 1 to 12 carbon atoms, an aromatic hydrocarbon group having 6 to 12 carbon atoms, $-OSO_2-R^{17}$, or $-SO_2-R^{18}$. Alternatively, two or more of $R^{12}$ to $R^{14}$ may taken together represent a ring. In addition, in a case where $R^{12}$ to $R^{14}$ are present in a plurality of number, a plurality of $R^{12}$s are each identical or different, a plurality of $R^{13}$s are each identical or different and a plurality of $R^{14}$s are each identical or different. Moreover, a part or all of hydrogen atoms included in the alkyl group and the aromatic hydrocarbon group are not substituted or substituted. $R^{17}$ and $R^{18}$ each independently represent an alkyl group having 1 to 12 carbon atoms, an alicyclic hydrocarbon group having 5 to 25 carbon atoms, or an aromatic hydrocarbon group having 6 to 12 carbon atoms. A part or all of hydrogen atoms included in the alkyl group, the alicyclic hydrocarbon group and the aromatic hydrocarbon group are not substituted or substituted. q1 to q3 are each independently an integer of 0 to 5.

In the above formula (4-2), $R^{15}$ represents a hydrogen atom, an alkyl group having 1 to 8 carbon atoms, or an aromatic hydrocarbon group having 6 to 8 carbon atoms. A part or all of hydrogen atoms included in the alkyl group and the aromatic hydrocarbon group are not substituted or substituted. Wherein, in a case where $R^{15}$ is present in a plurality of number, a plurality of $R^{15}$s are each identical or different, or a plurality of $R^{15}$s taken together represent a ring. $R^{16}$ represents a hydrogen atom, an alkyl group having 1 to 7 carbon atoms, or an aromatic hydrocarbon group having 6 to 7 carbon atoms. A part or all of hydrogen atoms included in the alkyl group and the aromatic hydrocarbon group are not substituted or substituted. Wherein, in a case where $R^{16}$ is present in a plurality of number, a plurality of $R^{16}$s are each identical or different, or a plurality of $R^{16}$s taken together represent a ring. q4 is an integer of 0 to 7, q5 is an integer of 0 to 6, and q6 is an integer of 0 to 3.

Examples of the alkyl group having 1 to 12 carbon atoms represented by $R^{12}$ to $R^{14}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethyl-hexyl group, and the like. In addition, the substituent which may be included in the alkyl group is exemplified by groups similar to those exemplified as monovalent organic groups represented by $R^2$ and $R^3$.

Examples of the aromatic hydrocarbon group having 6 to 12 carbon atoms represented by $R^{12}$ to $R^{14}$ include a phenyl group, a naphthyl group, and the like.

Examples of the alkyl group having 1 to 12 carbon atoms represented by $R^{17}$ and $R^{18}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethyl-hexyl group, and the like.

Examples of the alicyclic hydrocarbon group having 5 to 25 carbon atoms represented by $R^{17}$ and $R^{18}$ include a cyclopentyl group, a cyclohexyl group, a cyclooctyl group, an adamantyl group, a norbonyl group, and the like.

Examples of the aromatic hydrocarbon group having 6 to 12 carbon atoms represented by $R^{17}$ and $R^{18}$ include a phenyl group, a naphthyl group, and the like.

Examples of the alkyl group having 1 to 8 carbon atoms represented by $R^{15}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a 2-ethylhexyl group, and the like.

Examples of the aromatic hydrocarbon group having 6 to 8 carbon atoms represented by $R^{15}$ include a phenyl group, and the like.

Examples of the alkyl group having 1 to 7 carbon atoms represented by $R^{16}$ include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, and the like.

Examples of the aromatic hydrocarbon group having 6 to 7 carbon atoms represented by $R^{16}$ include a phenyl group, and the like.

The substituent which may be included in the alkyl group and the aromatic hydrocarbon group in the above formulae (4-1) and (4-2) illustrated in the foregoing is exemplified by a halogen atom such as fluorine, chlorine, bromine or iodine; a hydroxyl group; as well as an organic group such as a cyano group, a thiol group, an aromatic hydrocarbon group, an alkenyl group, an alkyl group that includes a hetero atom (for example, a halogen atom, an oxygen atom, a nitrogen atom, a sulfur atom, a phosphorus atom, a silicon atom, etc.) and an alicyclic hydrocarbon group, and the like. Moreover, the substituent which may be included in the alkyl group is exemplified by a keto group derived by substituting two hydrogen atoms on a single carbon by one oxygen atom. These substituents may be present in any number within a structurally acceptable range.

Among the sulfonium cations represented by the above formulae (4-1) and (4-2), those represented by the following formulae (1-1) to (1-13) are preferred. Of these, those represented by the following formulae (1-1), (1-6) to (1-13) are more preferred.

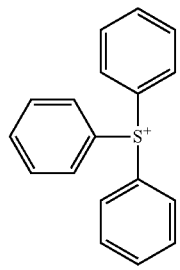

(i-1)

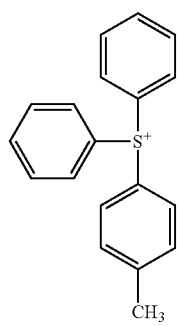

(i-2)

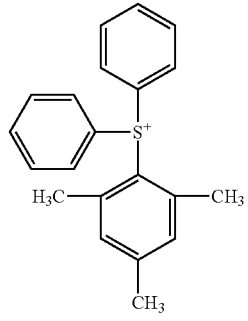

(i-3)

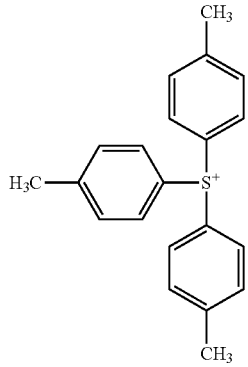

(i-4)

(i-5) 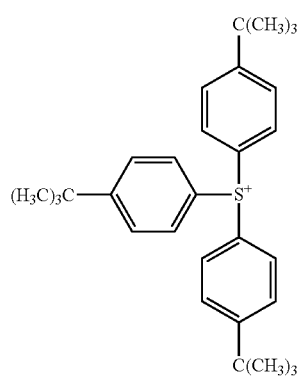
(i-6) 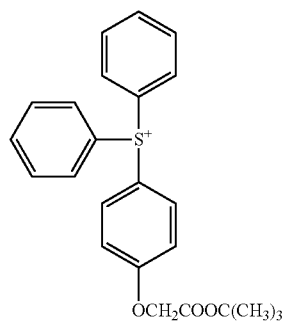
(i-7) 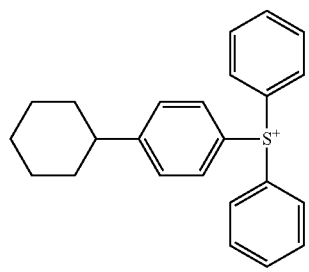
(i-8) 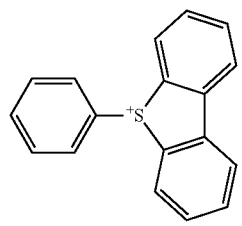
(i-9) 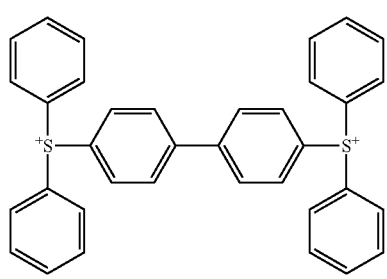
(i-10) 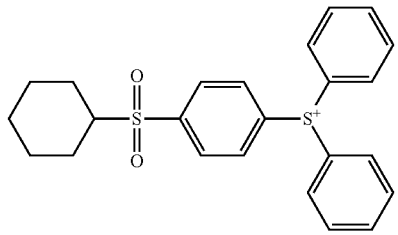
(i-11) 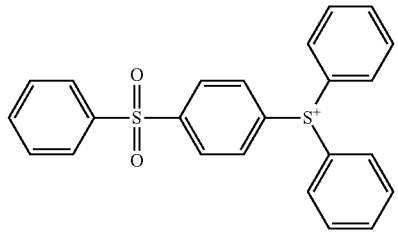
(i-12) 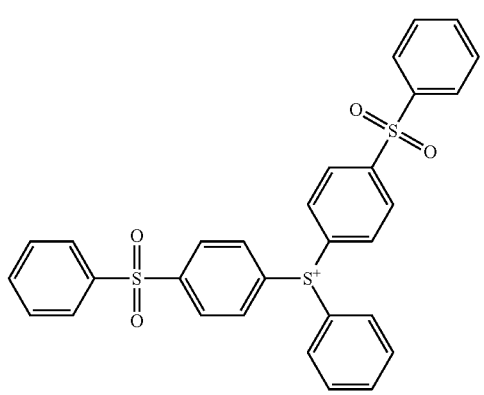
(i-13) 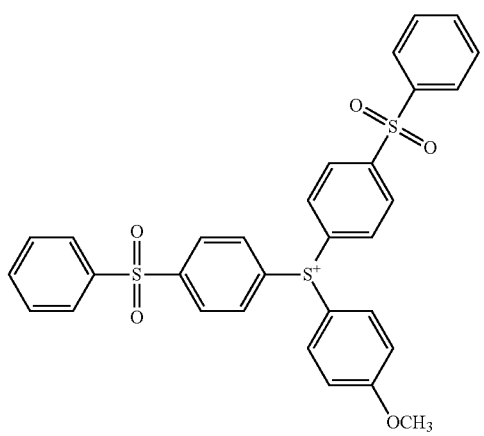
Examples of the alkyl group having 1 to 10 carbon atoms represented by $R^{10}$ and $R^{11}$ in the above formula (5) include a methyl group, an ethyl group, a n-propyl group, an i-propyl group, a n-butyl group, a t-butyl group, a n-pentyl group, an i-pentyl group, a n-hexyl group, an i-hexyl group, a n-heptyl group, a n-octyl group, an i-octyl group, a n-nonyl group, a n-decyl group, a 2-ethylhexyl group, and the like.

Examples of the aromatic hydrocarbon group having 6 to 18 carbon atoms represented by $R^{10}$ and $R^{11}$ include a phenyl group, a 1-naphthyl group, a 2-naphthyl group, a 1-anthryl group, a 1-phenanthryl group, and the like.

The substituent which may be included in the alkyl group and the aromatic hydrocarbon group in the above formula (5) is exemplified by groups similar to those exemplified as the substituent which may be included in the alkyl group and the hydrocarbon group in the above formulae (4-1) and (4-2).

Among the onium cations represented by the above formula (5), an onium cation represented by the following formula (5-1) is preferred.

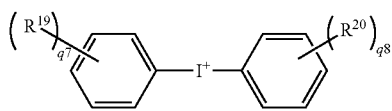

(5-1)

In the above formula (5-1), $R^{19}$ and $R^{20}$ each independently represent a hydrogen atom, an alkyl group having 1 to 12 carbon atoms, or an aromatic hydrocarbon group having 6 to 12 carbon atoms; q7 and q8 are each independently an integer of 0 to 5, wherein in a case where $R^{19}$ and $R^{20}$ are present in a plurality of number, a plurality of $R^{19}$s are each identical or different and a plurality of $R^{20}$s are each identical or different. Alternatively, two or more of $R^{19}$ and $R^{20}$ may taken together represent a ring.

Examples of the alkyl group having 1 to 12 carbon atoms represented by $R^{19}$ and $R^{20}$ include a methyl group, an ethyl group, a n-propyl group, an i-propyl group, a n-butyl group, a 2-methylpropyl group, a 1-methylpropyl group, a t-butyl group, and the like.

Examples of the aromatic hydrocarbon group having 6 to 12 carbon atoms represented by $R^{19}$ and $R^{20}$ include a phenyl group, a naphthyl group, and the like.

Among the iodonium cations represented by the above formula (5-1), those represented by the following formulae (ii-1) to (ii-3) are preferred. Of these, the iodonium cation represented by the formula (ii-1) or (ii-2) is more preferred.

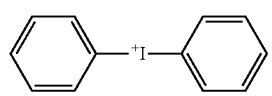

(ii-1)

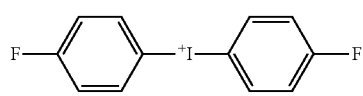

(ii-2)

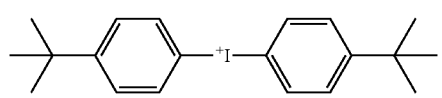

(ii-3)

The monovalent onium cation represented by M+ in the compound (A) may be produced according to a general method such as, for example, a method described in Advances in Polymer Science, Vol. 62, pp. 1-48 (1984).

The compound (A) may be constituted with a combination of the anion and the cation. It is to be noted that the compound (A) may be used either alone, or as a mixture of two or more thereof.

The radiation-sensitive resin composition may be used in combination with other acid generating agent except for the compound (A). Such other acid generating agent is exemplified by an onium salt compound (excluding the compound (A)), a halogen-containing compound, a diazo ketone compound, a sulfone compound, a sulfonic acid compound, and the like. These other acid generating agent may be used either alone, or as a mixture of two or more types thereof.

Examples of the onium salt compound include iodonium salts, sulfonium salts, phosphonium salts, diazonium salts, pyridinium salts, and the like.

Examples of the halogen-containing compound include haloalkyl group-containing hydrocarbon compounds, haloalkyl group-containing heterocyclic compounds, and the like.

Examples of the diazo ketone compound include 1,3-diketo-2-diazo compound, diazo benzoquinone compound, diazo naphthoquinone compound, and the like.

Examples of the sulfone compound include β-ketosulfone, β-sulfonylsulfone, α-diazo compounds of these compounds, and the like.

Examples of the sulfonic acid compound include alkylsulfonic acid esters, alkylsulfonic acid imide, haloalkyl sulfonic acid esters, arylsulfonic acid esters, imino sulfonate, and the like.

The proportion of the compound (A) used in the radiation-sensitive resin composition with respect to 100 parts by mass of the polymer (B) described later is preferably 1 part by mass to 30 parts by mass, and more preferably 5 parts by mass to 20 parts by mass. The proportion of the other acid generating agent used with respect to the entire acid generating agents including the compound (A) is preferably no greater than 99% by mass, and more preferably no greater than 75% by mass. The total amount of the compound (A) and the other acid generating agent used is, in light of securement of sensitivity and developability as a resist, typically 2 parts by mass to 35 parts by mass, and preferably 7 parts by mass to 25 parts by mass with respect to 100 parts by mass of the polymer (B). When the total amount is less than 2 parts by mass, sensitivity and developability tend to be deteriorated. On the other hand, when the total amount exceeds 35 parts by mass, transparency to radioactive rays decreases, whereby obtaining a favorable resist pattern may fail.

Synthesis Method of the Compound (A)

The compound (A) may be synthesized according to, for example, a synthesis method described below, and the like.

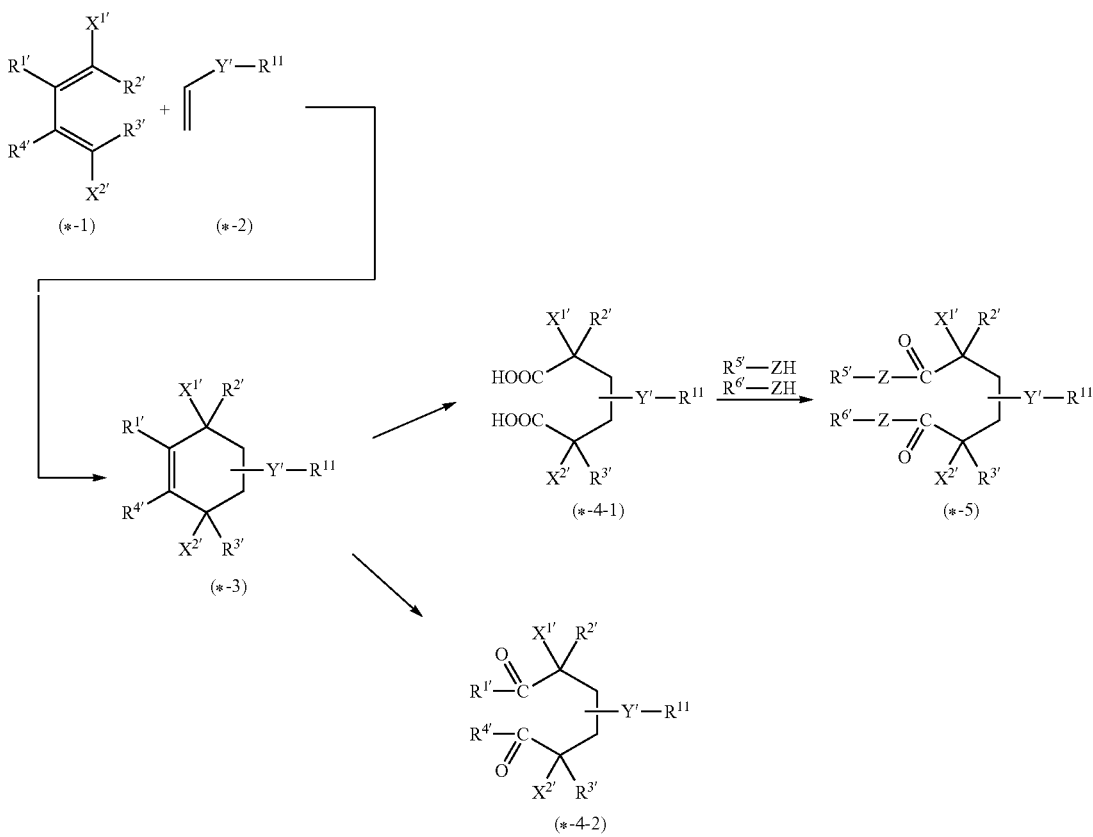

In the above formulae, $X^{1'}$, $X^{2'}$, $R^{1'}$, $R^{2'}$, $R^{3'}$, $R^{4'}$, $Y'$ and $R^{11}$ are as defined in the above formula (3); $R^{5'}$ and $R^{6'}$ each independently represent a monovalent organic group; and Z represents —O— or —NH—.

In a case where $R^{11}$ represents a chlorine atom, a bromine atom or an iodine atom, during any stage in the reaction formula, or after synthesizing (*-5), an oxidization reaction following a sulfination reaction is carried out, whereby —$SO_3^-M^+$ can be yielded. $M^+$ represents a monovalent onium cation. Also, as needed, the structure of $M^+$ may be converted into other structure by a salt exchange reaction during the synthesis.

Examples of the sulfinating agent used in the sulfination reaction include lithium dithionite, sodium dithionite, potassium dithionite, ammonium dithionite, lithium hydroxymethanesulfinate, sodium hydroxymethanesulfinate, potassium hydroxymethanesulfinate, ammonium hydroxymethanesulfinate, lithium sulfite, sodium sulfite, potassium sulfite, ammonium sulfite, lithium bisulfite, sodium bisulfite, potassium bisulfite, ammonium bisulfite, and the like. Of these, sodium dithionite, and potassium dithionite are preferred, and sodium dithionite is more preferred.

Examples of the oxidizing agent used in the oxidization reaction include hydrogen peroxide, meta-chloroperbenzoic acid, t-butylhydroperoxide, potassium peroxysulfuric acid, potassium permanganate, sodium perborate, sodium metaiodate, chromate, sodium dichromate, halogen, iodobenzene dichloride, iodobenzene diacetate, osmium (VIII) oxide, ruthenium (VIII) oxide, sodium hypochlorite, sodium chlorite, oxygen gas, ozone gas, and the like. Of these, hydrogen peroxide, meta-chloroperbenzoic acid and t-butylhydroperoxide are preferred. It is to be noted that transition metal catalyst may be used as an additive, in combination with the oxidizing agent. Examples of the transition metal catalyst include disodium tungstate, iron (III) chloride, ruthenium (III) chloride, selenium (IV) oxide, and the like. Of these, disodium tungstate is preferred.

Synthesis Method of Compound (*-3)

The compound (*-3) may be synthesized by, for example, a Diels-Alder reaction of the compound (*-1) and the compound (*-2). In this method, a solvent (hereinafter, may be also referred to as "solvent (α)") may or may not be used. In order to accelerate the reaction, heating, compression, and/or addition of Lewis acid may be also conducted. After the completion of the reaction, purification carried out if necessary by distillation, recrystallization, column chromatography, washing by way of liquid-liquid separation, washing by way of solid-liquid separation, etc., may give the compound (*-3).

The compound (*-3) obtained in this step as an intermediate compound is preferably the compound represented by the above formula (3).

In the above formula (3), $R^{1'}$ and $R^{4'}$ each independently represent a hydrogen atom, a hydroxyl group or a monovalent organic group; $R^{2'}$ and $R^{3'}$ each independently represent a hydrogen atom or a monovalent organic group; $R^{11}$ represents a bromine atom, a chlorine atom or an iodine atom; $X^{1'}$ and $X^{2'}$ each independently represent a hydrogen atom, a hydroxyl group, a thiol group, a sulfonyl group or a monovalent organic group, or $X^{1'}$ and $X^{2'}$ taken together represent —S—, —O—, —$SO_2$—, an alkanediyl group having 1 to 10 carbon atoms or a combined group thereof; Y' represents an alkanediyl group having 1 to 10 carbon atoms that is not substituted or substituted with a fluorine atom; and n' is an integer of 1 to 4, wherein in the case where n' is 2 or greater, a plurality of Y's are each identical or different and a plurality of $R^{11}$s are each identical or different.

The monovalent organic group represented by $R^{1'}$ and $R^{4'}$ is exemplified by groups similar to those exemplified as monovalent organic groups represented by $R^1$ and $R^4$ in the above formula (1), and preferred groups include similar ones as exemplified.

The monovalent organic group represented by $R^{2'}$ and $R^{3'}$ is exemplified by groups similar to those exemplified as monovalent organic groups represented by $R^2$ and $R^3$ in the above formula (1).

The monovalent organic group represented by $X^1$ and $X^2$ is exemplified by groups similar to those exemplified as monovalent organic groups represented by $X^1$ and $X^2$ in the above formula (1).

The group which may be taken together represented by $X^{1'}$ and $X^{2'}$ is exemplified by groups similar to those exemplified as the groups which may be taken together represented by $X^1$ and $X^2$ in the above formula (1), and preferred groups include similar ones as exemplified.

The alkanediyl group having 1 to 10 carbon atoms in the alkanediyl group having 1 to 10 carbon atoms that is not substituted or substituted with a fluorine atom represented by Y' is exemplified by groups similar to those exemplified as the alkanediyl group having 1 to 10 carbon atoms which may be taken together represented by $X^1$ and $X^2$ in the above formula (1). Also, preferred alkanediyl groups include similar ones as exemplified.

n' is preferably 1 to 2, and more preferably 1.

Examples of the compound represented by the above formula (3) include compounds represented by the following formulae (3-1) to (3-12), and the like.

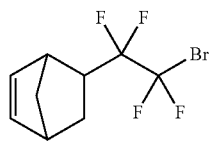

(3-1)

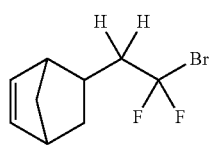

(3-2)

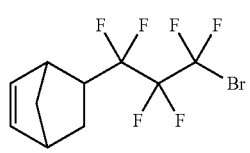

(3-3)

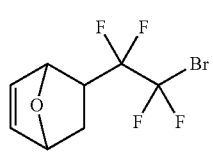

(3-4)

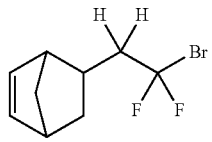

(3-5)

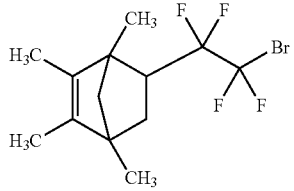

(3-6)

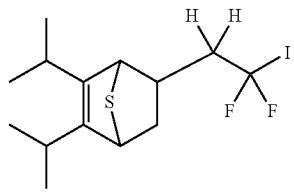

(3-7)

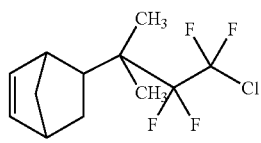

(3-8)

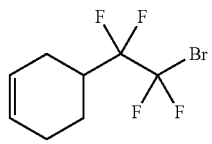

(3-9)

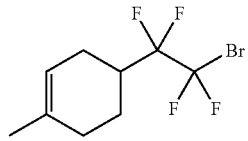

(3-10)

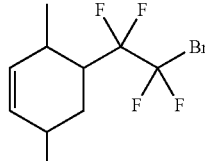

(3-11)

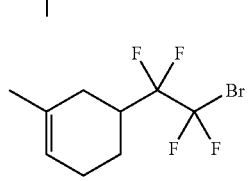

(3-12)

Of these, compounds represented by the above formulae (3-1), and (3-9) to (3-12) are preferred.

Examples of the solvent (α) include heptane, hexane, cyclohexane, benzene, toluene, diethyl ether, diisopropyl ether, dichloromethane, chloroform, carbon tetrachloride, tetrahydrofuran, ethyl acetate, dimethyl formamide, acetonitrile, dimethylacetamide, N-methylpyrrolidone, dioxane, acetone, methylethyl ketone, methylisobutyl ketone, water, and the like. It is to be noted that the solvent (α) may be used either alone or two or more types thereof may be used.

Synthesis Method of Compound (*-4-1) and Compound (*-4-2)

The compound (*-4-1) and the compound (*-4-2) may be synthesized by, for example, an oxidative cleavage reaction of an olefin of the compound (*-3), or an oxidative cleavage reaction of a diol following formation of the diol from an olefin. In a case in which $R^{1'}$ and $R^{2'}$ represent a hydrogen atom, the compound (*-4-1) is synthesized, whereas in a case in which $R^{1'}$ and $R^{2'}$ represent a monovalent organic group, the compound (*-4-2) is synthesized. In this method, the solvent (α) may or may not be used. After the completion of the reaction, purification carried out if necessary by distillation, recrystallization, column chromatography, washing by way of liquid-liquid separation, washing by way of solid-liquid separation, etc., may give the compound (*-4-1) and the compound (*-4-2).

With respect to the process of carrying out the oxidative cleavage reaction of an olefin, for example, a process in which at least an equivalent amount of ruthenium tetraoxide is used, a process in which a catalytic amount of a ruthenium compound and a reoxidizing agent are used, a process in which ozone oxidization is adopted, a process in which potassium permanganate oxidation is adopted, or the like may be employed.

The ruthenium compound is preferably ruthenium trichloride, and the reoxidizing agent is preferably sodium periodate, periodic acid or hydrogen peroxide.

With respect to the reaction of forming diol from an olefin, for example, a process in which potassium permanganate oxidation is adopted, a process in which osmium oxidization is adopted, a process in which hydrolysis of an epoxide is employed, or the like may be employed.

With respect to the oxidative cleavage reaction of the diol, for example, a process in which oxidization is carried out using sodium periodate or periodic acid, a process in which potassium permanganate oxidation is adopted, a process in which lead tetraacetate is used, or the like may be employed.

Synthesis Method of Compound (*-5)

The compound (*-5) may be synthesized by, for example, esterification and/or amidation of the compound (*-4-1). In this method, the solvent (α) may or may not be used. In addition, In order to accelerate the reaction, a base compound (hereinafter, may be also referred to as "base (β)") and/or an acidic compound (hereinafter, may be also referred to as "acid (γ)") may be also added. After the completion of the reaction, purification carried out if necessary by distillation, recrystallization, column chromatography, washing by way of liquid-liquid separation, washing by way of solid-liquid separation, etc., may give the compound (*-5).

Examples of the base (β) include trimethylamine, triethylamine, tripropylamine, tributylamine, diisopropylethylamine, diisopropylamine, dicyclohexylamine, 1-methylpiperidine, 1-methylpyrrolidine, quinuclidine, 1,4-diazabicyclo[2.2.2]octane, 1,8-diazabicyclo[5.4.0]undec-7-ene, pyridine, 4-dimethylaminopyridine, 4-methylpyridine, 2,6-dimethylpyridine, 2,6-diisopropylpyridine, 2,6-di-t-butylpyridine, lithium hydroxide, sodium hydroxide, potassium hydroxide, sodium carbonate, potassium carbonate, cesium carbonate, sodium bicarbonate, potassium bicarbonate, lithium, sodium, potassium, lithium hydride, sodium hydride, potassium hydride, calcium hydride, lithium diisopropylamide, n-butyllithium, s-butyllithium, t-butyllithium, sodium-t-butoxide, potassium-t-butoxide, and the like. It is to be noted that two ore more types of these may be used.

Examples of the acid (γ) include sulfuric acid, hydrochloric acid, nitric acid, sulfurous acid, nitrous acid, perchloric acid, acetic acid, oxalic acid, camphorsulfonic acid, benzenesulfonic acid, paratoluenesulfonic acid, trifluoroacetic acid, and the like. It is to be noted that two ore more types of these may be used.

With respect to the esterification reaction, for example, a process in which the compound (*-4-1) is allowed to react with an alcohol compound to convert the compound (*-4-1) into an acid halide, and then the product is allowed to react with the alcohol compound, or the like may be employed.

With respect to the amidation reaction, for example, a process in which the compound (*-4-1) is allowed to react with an amine compound to convert the compound (*-4-1) into an acid halide, and then the product is allowed to react with the amine compound, or the like may be employed.

Polymer (B)

The polymer (B) contained in the radiation-sensitive resin composition includes a structural unit whose solubility in an alkaline developer solution increases by an action of (b1) an acid (hereinafter, may be also referred to as "structural unit (b1)"). In other words, the polymer (B) is a resin that has an acid-labile group and is insoluble or hardly soluble in an alkali, and that turns to be soluble in an alkali when the acid-labile group is dissociated. It is to be noted that the phrase "being insoluble or hardly soluble in an alkali" as referred to in the embodiment of the present invention means to have a property that in a case in which a film produced using only the polymer (B) is developed in place of a resist film under alkali development conditions employed when resist patterns are formed from the resist film which had been formed with the radiation-sensitive resin composition, no less than 50% of the initial film thickness of the film remains after the development. In addition, it is preferred that the polymer (B) further includes (b2) a structural unit having a lactone structure or a cyclic structure carbonate and/or (b3) a structural unit having a polar group. Hereinafter, each structural unit will be described in detail.

Structural Unit (b1)

The structural unit (b1) is exemplified by a structural unit represented by the following formula (6).

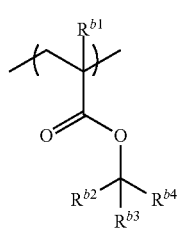

(6)

In the above formula (6), $R^{b1}$ represents a hydrogen atom or a methyl group; $R^{b2}$ to $R^{b4}$ each independently represent an alkyl group having 1 to 4 carbon atoms or an alicyclic hydrocarbon group having 4 to 20 carbon atoms. Alternatively, $R^{b3}$ and $R^{b4}$ may taken together represent a divalent alicyclic hydrocarbon group having 4 to 20 carbon atoms together with the carbon atom to which $R^{b3}$ and $R^{b4}$ bond.

Examples of the alkyl group having 1 to 4 carbon atoms include a methyl group, an ethyl group, a n-propyl group, an i-propyl group, a n-butyl group, a 2-methylpropyl group, a 1-methylpropyl group, a t-butyl group, and the like.

The alicyclic hydrocarbon group having 4 to 20 carbon atoms, or the alicyclic hydrocarbon group having 4 to 20 carbon atoms taken together represented by $R^{b3}$ and $R^{b4}$ together with the carbon atom to which $R^{b3}$ and $R^{b4}$ bond is exemplified by a having a bridged skeleton such as an adamantane skeleton or a norbornane skeleton; and a monocyclic alicyclic group having a cycloalkane skeleton such as cyclopentane or cyclohexane. In addition, these groups may be substituted with, for example, one or more types of saturated hydrocarbon group having 1 to 10 carbon atoms.

The structural unit (b1) is preferably represented by the following formulae.

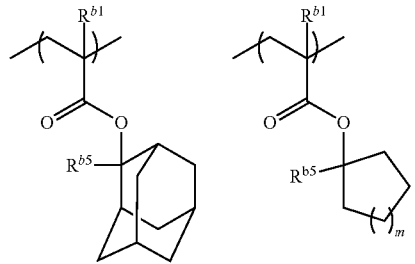

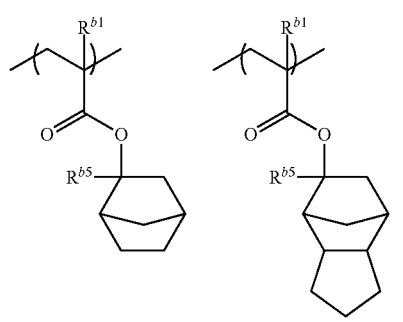

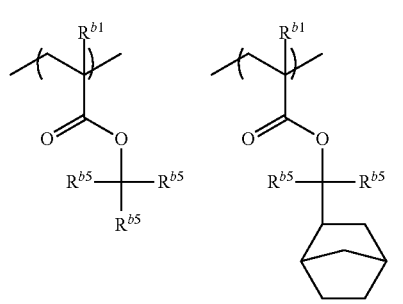

In the above formula, $R^{b1}$ is as defined in the above formula (6); $R^{b5}$ represents an alkyl group having 1 to 4 carbon atoms; and m is an integer of 1 to 6.

Of these, structural units represented by the following formulae (6-1) to (6-20) are more preferred, and structural units represented by the formulae (6-2), (6-3), (6-4), (6-11), (6-12) and (6-13) are still more preferred.

(6-1)
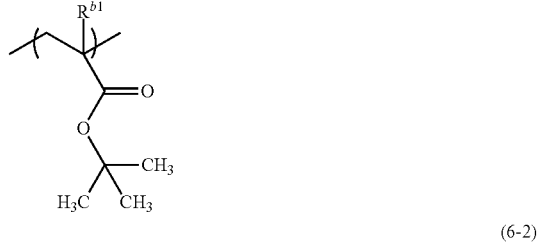

(6-2)
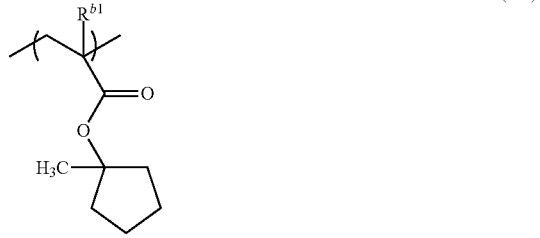

(6-3)
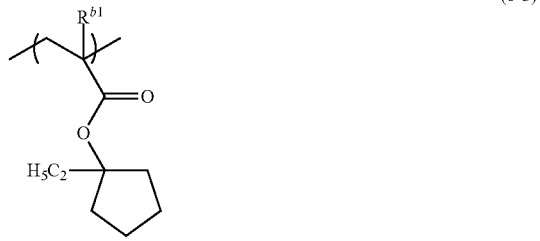

(6-4)
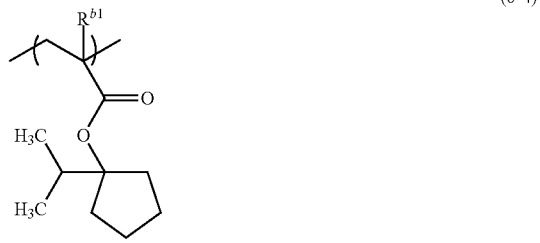

(6-5)
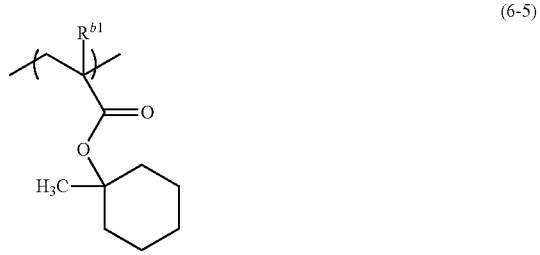

(6-6)
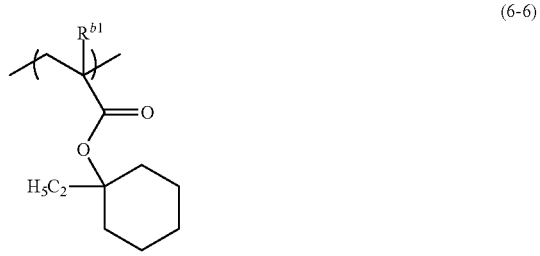

(6-7) 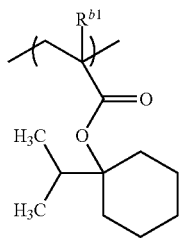
(6-8) 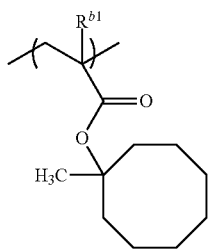
(6-9) 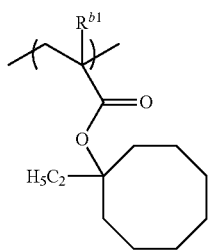
(6-10) 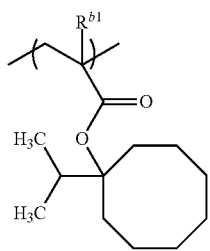
(6-11) 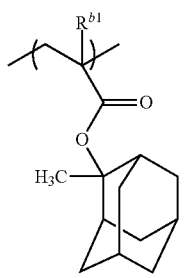
(6-12) 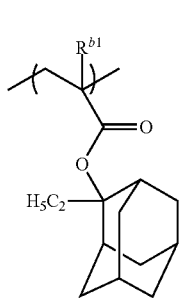
(6-13) 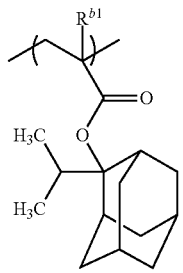
(6-14) 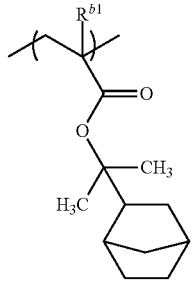
(6-15) 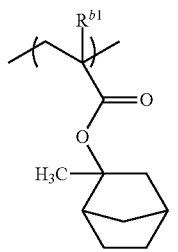
(6-16) 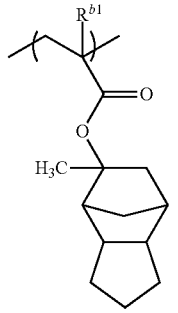
(6-17) 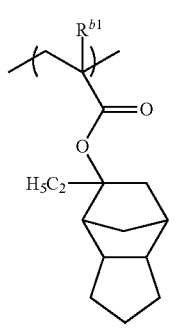

-continued (6-18)
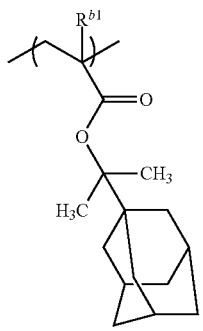

(6-19)
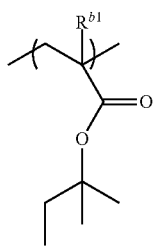

(6-20)
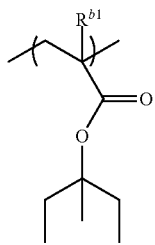

In the above formulae, $R^{b1}$ is as defined in the above formula (6).

The content of the structural unit (b1) in the polymer (B) is preferably 5 mol % to 80 mol %, more preferably 10 mol % to 80 mol %, and still more preferably 20 mol % to 70 mol %. When the content of the structural unit (b1) exceeds 80 mol %, adhesiveness of the resist film is impaired, and thus pattern collapse and/or pattern peeling may occur. It is to be noted that the polymer (B) may include one, or two or more types of the structural unit (b1).

Examples of a monomer that gives the structural unit (b1) include (meth)acrylic acid-bicyclo[2.2.1]hept-2-yl ester, (meth)acrylic acid-bicyclo[2.2.2]oct-2-yl ester, (meth)acrylic acid-tricyclo[5.2.1.0$^{2,6}$]dec-7-yl ester, (meth)acrylic acid-tricyclo[3.3.1.1$^{3,7}$]dec-1-yl ester, (meth)acrylic acid-tricyclo[3.3.1.1$^{3,7}$]dec-2-yl ester, and the like.

Structural Unit (b2)

It is preferred that the polymer (B) further includes the structural unit (b2) having a lactone structure or a cyclic carbonate structure. When the structural unit (b2) is included, adhesiveness of the resist film to a substrate can be improved.

Examples of the structural unit (b2) are represented by the following formulae, and the like.

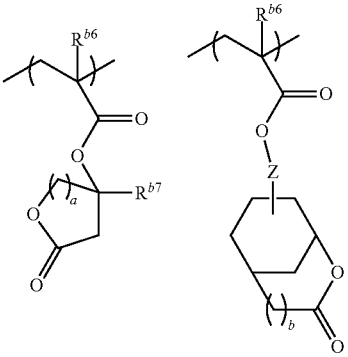

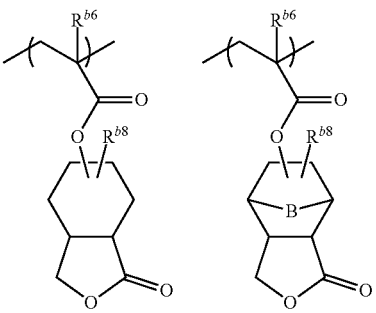

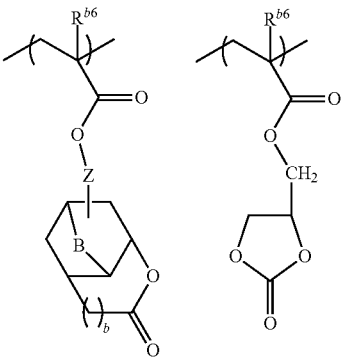

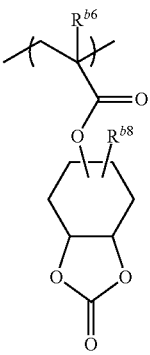

In the above formulae, $R^{b6}$ represents a hydrogen atom or a methyl group; $R^{b7}$ represents a hydrogen atom or a methyl group; $R^{b8}$ represents a hydrogen atom or a methoxy group; Z represents a single bond or a methylene group; B represents a methylene group or an oxygen atom; and a and b are 0 or 1.

The (b2) structural unit is preferably represented by the following formulae.

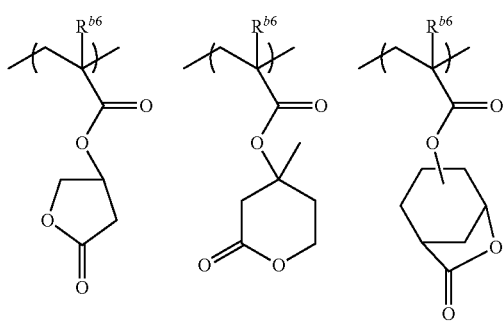

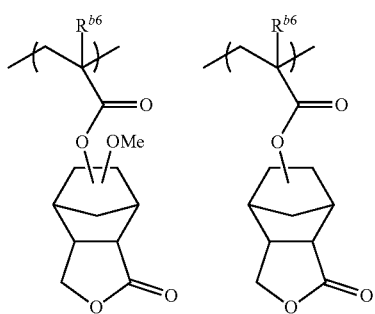

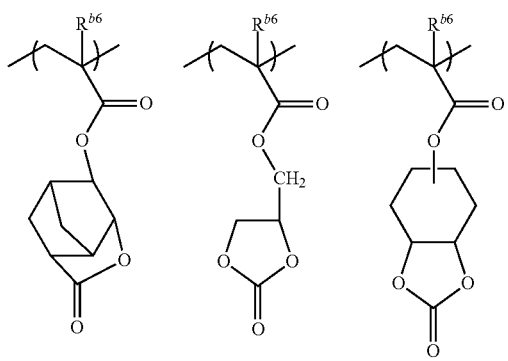

In the above formula, $R^{b6}$ represents a hydrogen atom or a methyl group.

The content of the structural unit (b2) in the polymer (B) is preferably 0 mol % to 70 mol %, and more preferably 10 mol % to 60 mol %. When the content falls within such a range, developability and LWR as a resist are improved, and betterment of defectiveness and low temperature PEB dependency is enabled. On the other hand, when the content exceeds 70 mol %, resolving ability and LWR as a resist may be deteriorated.

A monomer that gives the structural unit (III) is exemplified by monomers described in the pamphlet of PCT Structural Unit (b3)

It is preferred that the polymer (B) further includes the structural unit (b3) represented by the following formula. The term "polar group" as referred to herein is exemplified by a hydroxyl group, a carboxyl group, keto group, a sulfonamide group, an amino group, an amide group, and a cyano group.

Examples of the structural unit (b3) are represented by the following formulae, and the like.

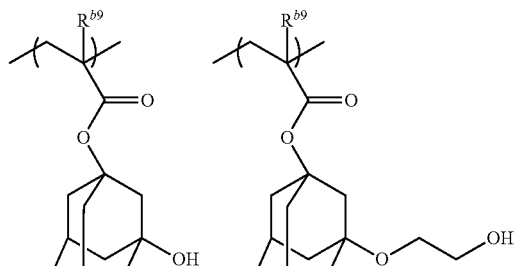

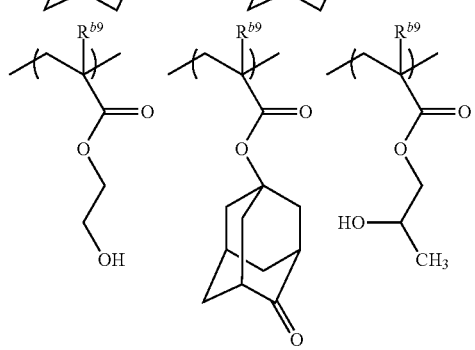

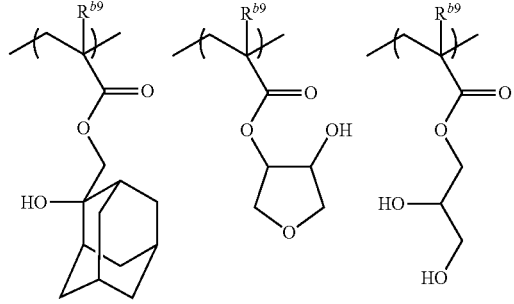

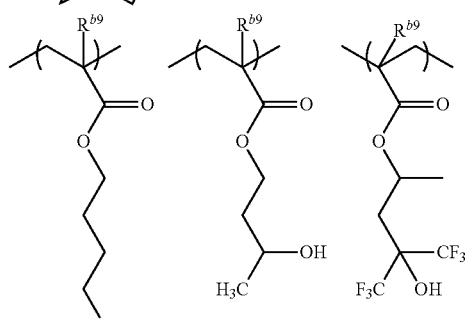

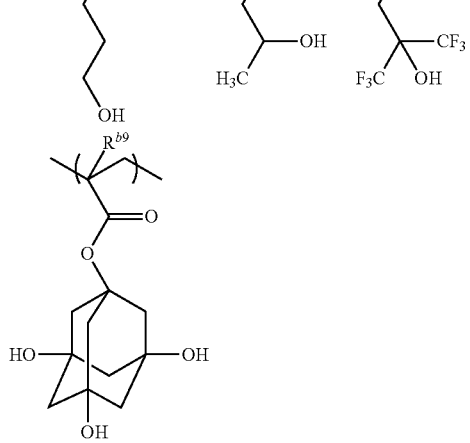

-continued

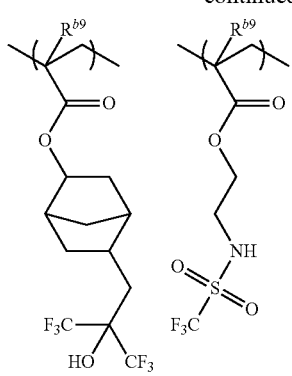

In the above formulae, $R^{b9}$ represents a hydrogen atom or a methyl group.

The structural unit (b3) is preferably represented by the following formulae.

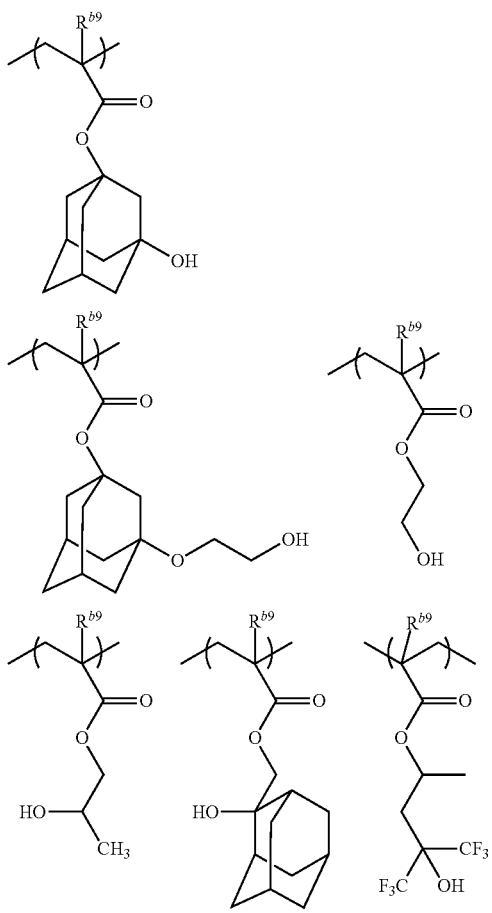

In the above formula, $R^{b9}$ represents a hydrogen atom or a methyl group.

The content of the structural unit (b3) in the polymer (B) is preferably 0 mol % to 30 mol %, and more preferably 5 mol % to 20 mol %. It is to be noted that one, or two or more types of the polymer (B) may be used in the radiation-sensitive resin composition.

Synthesis Method of Polymer (B)

The polymer (B) may be synthesized according to a common procedure such as radical polymerization. The polymer (A) is preferably synthesized according to a method such as, e.g.:

a method in which a solution containing a monomer and a radical initiator is added dropwise to a solution containing a reaction solvent or a monomer to permit a polymerization reaction; or a method in which a solution containing a monomer, and a solution containing a radical initiator are each separately added dropwise to a solution containing a reaction solvent or a monomer to permit a polymerization reaction;

a method in which a plurality of solutions each containing a monomer, and a solution containing a radical initiator are each separately added dropwise to a solution containing a reaction solvent or a monomer to permit a polymerization reaction.

It is to be noted that when the reaction is allowed by adding a monomer solution dropwise to a monomer solution, the amount of the monomer in the monomer solution added is preferably no less than 30 mol %, more preferably no less than 50 mol %, and still more preferably no less than 70 mol % with respect to the total amount of the monomers used in the polymerization.

The reaction temperature in these methods may be determined ad libitum depending of the type of the initiator species. The reaction temperature is usually 30° C. to 180° C., preferably 40° C. to 160° C., and more preferably 50° C. to 140° C. The time period for the dropwise addition may vary depending on the conditions such as the reaction temperature, the type of the initiator and the monomer to be reacted, but is usually 30 min to 8 hrs, preferably 45 min to 6 hrs, and more preferably 1 hour to 5 hrs. Further, the total reaction time period including the time period for dropwise addition may also vary depending on the conditions similarly to the time period for the dropwise addition, and is typically 30 min to 8 hrs, preferably 45 min to 7 hrs, and more preferably 1 hour to 6 hrs.

The radical initiator for use in the polymerization is exemplified by azobisisobutyronitrile (AIBN), 2,2'-azobis(4-methoxy-2,4-dimethyl valeronitrile), 2,2'-azobis(2-cyclopropyl propionitrile), 2,2'-azobis(2,4-dimethyl valeronitrile), and the like. These initiators may be used either alone or as a mixture of two or more thereof.

Examples of the solvent for use in the polymerization include:

alcohols such as methanol, ethanol, 1-propanol, 2-propanol and 4-methyl-2-pentanol;

ketones such as acetone, 2-butanone, 4-methyl-2-pentanone and 2-heptanone;

saturated carboxylate esters such as ethyl acetate, n-butyl acetate, i-butyl acetate and methyl propionate;

alkanes such as n-pentane, n-hexane, n-heptane, n-octane, n-nonane and n-decane;

cycloalkanes such as cyclohexane, cycloheptane, cyclooctane, decalin and norbornane;

aromatic hydrocarbons such as benzene, toluene, xylene, ethylbenzene and cumene;

halogenated hydrocarbons such as chlorobutanes, bromohexanes, dichloroethanes, hexamethylenedibromide and chlorobenzene;

ethers such as tetrahydrofuran, dimethoxy ethanes and diethoxyethanes; and the like. These solvents may be used either alone, or two or more types thereof may be used in combination.

The resin obtained by the polymerization reaction may be recovered preferably by a reprecipitation technique. More specifically, after the polymerization reaction is completed, the polymerization mixture is charged into a solvent for reprecipitation, whereby a target resin is recovered in the form of powder. As the reprecipitation solvent, an alcohol, an alkane or the like may be used either alone or as a mixture of two or more thereof. Alternatively to the reprecipitation technique, liquid separating operation, column operation, ultrafiltration operation or the like may be employed to recover the resin through eliminating low molecular components such as monomers and oligomers.

The polystyrene equivalent weight average molecular weight (Mw) of the polymer (B) as determined by gel permeation chromatography (GPC) is not particularly limited, and preferably no less than 1,000 and no greater than 500,000, more preferably no less than 2,000 and no greater than 400,000, and particularly preferably no less than 3,000 and no greater than 300,000. When the Mw of the polymer (B) is less than 1,000, heat resistance is likely to be inferior when formed into a resist. On the other hand, when the Mw of the polymer (B) exceeds 500,000, developability is likely to be inferior when formed into a resist.

Also, the ratio (Mw/Mn) of Mw to the polystyrene equivalent number average molecular weight (Mn) as determined by GPC of the polymer (B) is typically 1 or greater and 5 or less, preferably 1 or greater and 3 or less, and more preferably 1 or greater and 2 or less. When the ratio Mw/Mn falls within such a range, a photoresist film that is superior in resolving performances may be obtained.

Mw and Mn as referred to herein mean values determined by GPC using GPC columns manufactured by Tosoh Corporation ("G2000HXL"×2, "G3000HXL"×1 and "G4000HXL"×1), under conditions involving a flow rate of 1.0 mL/min, an elution solvent of tetrahydrofuran and a column temperature of 40° C., and with monodisperse polystyrene as a standard.

Polymer (C)

The radiation-sensitive resin composition may contain (C) a fluorine atom-containing polymer as a favorable component. When the radiation-sensitive composition contains the polymer (C), hydrophobicity of the resist film is improved, and elution of substances can be favorably suppressed even in cases in which liquid immersion lithography is carried out. In addition, a receding contact angle of the liquid immersion liquid with respect to the resist film can be sufficiently increased, whereby an effect of preventing droplets from remaining even if exposure is carried out by high-speed scanning, and the like. Therefore, usability of the radiation-sensitive composition for liquid immersion lithography is improved.

Modes of the fluorine atom-containing polymer (C) may involve:

a structure in which a fluorinated alkyl group bonds to its main chain;

a structure in which a fluorinated alkyl group bonds to its side chain; and a structure in which a fluorinated alkyl group bonds to its main chain and a side chain.

Examples of the monomer that gives the structure in which a fluorinated alkyl group bonds to its main chain include α-trifluoromethyl acrylate compounds, β-trifluoromethyl acrylate compounds, α,β-trifluoromethyl acrylate compounds, compounds derived by substituting hydrogen atom of one or more types of vinyl moieties by a fluorinated alkyl group such as a trifluoromethyl group, and the like.

Examples of the monomer that gives the structure in which a fluorinated alkyl group bonds to its side chain include alicyclic olefin compounds such as norbornene having fluorinated alkyl group and/or a derivative thereof as a side chain, ester compounds of acrylic acid or methacrylic acid having a fluorinated alkyl group and/or a derivative thereof as a side chain, olefins having a fluorinated alkyl group and/or a derivative thereof as one or more types of side chain (a site excluding a double bond), and the like.

Examples of the monomer that gives the structure in which a fluorinated alkyl group bonds to its main chain and side chain include ester compounds of α-trifluoromethyl acrylic acid, β-trifluoromethyl acrylic acid, α,β-trifluoromethyl acrylic acid or the like with a fluorinated alkyl group and/or a derivative thereof as a side chain, compounds derived by substituting hydrogen of one or more types of vinyl moieties by a fluorinated alkyl group and substituting a side chain of the compound with a fluorinated alkyl group and/or a derivative thereof; alicyclic olefin compounds derived by substituting hydrogen bonded to one or more types of double bonds by a fluorinated alkyl group, etc., and having a fluorinated alkyl group and/or a derivative thereof as a side chain; and the like. The alicyclic olefin compound as referred to herein means a compound that includes a double bond in a part of its ring.

The polymer (C) preferably includes (c1) a structural unit represented by the following formula (7) and/or (c2) a structural unit represented by the formula (8). In addition, "other structural unit" except for the structural unit (c1) and the structural unit (c2) may be also included. Hereinafter, each structural unit will be described in detail.

Structural Unit (c1)

The structural unit (c1) is represented by the following formula (7).

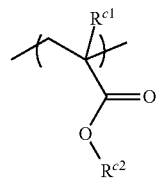

(7)

In the above formula (7), $R^{c1}$ represents a hydrogen atom, a fluorine atom, a methyl group or a trifluoromethyl group; $R^{c2}$ represents an alkyl group having 1 to 6 carbon atoms and having a fluorine atom, or a monovalent alicyclic hydrocarbon group having 4 to 20 carbon atoms and having a fluorine atom, wherein the a part or all of hydrogen atoms of the alkyl group and the alicyclic hydrocarbon group represented by $R^{c1}$ are not substituted or substituted.

Examples of the alkyl group having 1 to 6 carbon atoms include a methyl group, an ethyl group, a propyl group, a butyl group, and the like.

Examples of the monovalent alicyclic hydrocarbon group having 4 to 20 carbon atoms include a cyclopentyl group, a cyclopentylpropyl group, a cyclohexyl group, a cyclohexylmethyl group, a cycloheptyl group, a cyclooctyl group, a cyclooctylmethyl group, and the like.

Examples of the monomer that gives the structural unit (c1) include trifluoromethyl (meth)acrylate, 2,2,2-trifluoroethyl (meth)acrylate, perfluoroethyl (meth)acrylate, perfluoro n-propyl (meth)acrylate, perfluoro i-propyl (meth)acrylate, perfluoro n-butyl (meth)acrylate, perfluoro i-butyl (meth) acrylate, perfluoro t-butyl (meth)acrylate, perfluorocyclohexyl (meth)acrylate, 2-(1,1,1,3,3,3-hexafluoro)propyl (meth)acrylate, 1-(2,2,3,3,4,4,5,5-octafluoro)pentyl (meth)acrylate, 1-(2,2,3,3,4,4,5,5-octafluoro) hexyl (meth)acrylate, perfluorocyclohexylmethyl (meth)acrylate, 1-(2,2,3,3,3-pentafluoro)propyl (meth)acrylate, 1-(2,2,3,3,4,4,4-heptafluoro) penta (meth)acrylate, 1-(3,3,4,4,5,5,6,6,7,7,8,8,9,9,10,10,10-heptadecafluoro) decyl (meth)acrylate, 1-(5-trifluoromethyl-3,3,4,4,5,6,6,6-octafluoro)hexyl (meth)acrylate, and the like.

Examples of the structural unit (c1) are represented by the following formulae (7-1) and (7-2), and the like.

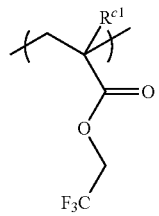

(7-1)

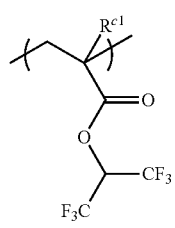

(7-2)

In the formulae (7-1) and (7-2), $R^{c1}$ is as defined in the above formula (7).

The content of the structural unit (c1) in the polymer (C) is preferably 10 mol % to 70 mol %, and more preferably 20 mol % to 60 mol %. It is to be noted that the polymer (C) may include one, or two or more types of the structural unit (c1).

Structural Unit (c2)

The structural unit (c2) is represented by the following formula (8).

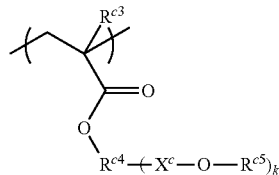

(8)

In the formula (8), $R^{c3}$ represents a hydrogen atom, a methyl group or a trifluoromethyl group; $R^{c4}$ represents a linking group having a valency of (k+1); $X^c$ represents a divalent linking group having a fluorine atom; $R^{c5}$ represents a hydrogen atom or a monovalent organic group; and k is an integer of 1 to 3, wherein in a case where k is 2 or 3, a plurality of Xs are each identical or different and a plurality of $R^{c5}$s are each identical or different.

In the above formula (8), examples of the linking group having a valency of (k+1) represented by $R^{c4}$ include a chain hydrocarbon group having 1 to 30 carbon atoms, an alicyclic hydrocarbon group having 3 to 30 carbon atoms, an aromatic hydrocarbon group having 6 to 30 carbon atoms, or a group derived from any of these groups by combining with an oxygen atom, a sulfur atom, an ether group, an ester group, a carbonyl group, an imino group, an amide group or a combination thereof. In addition, the linking group having a valency of (k+1) does not have or has a substituent.

Examples of the chain hydrocarbon group having 1 to 30 carbon atoms include groups derived from any of hydrocarbons such as methane, ethane, propane, butane, pentane, hexane, heptane, decane, icosane and triacontane by removing (k+1) hydrogen atoms therefrom.

Examples of the alicyclic hydrocarbon group having 3 to 30 carbon atoms include groups derived from any of the following hydrocarbons by removing (k+1) hydrogen atoms therefrom:

monocyclic saturated hydrocarbons such as cyclopropane, cyclobutane, cyclopentane, cyclohexane, cycloheptane, cyclooctane, cyclodecane, methylcyclohexane and ethylcyclohexane;

monocyclic unsaturated hydrocarbons such as cyclobutene, cyclopentene, cyclohexene, cycloheptene, cyclooctene, cyclodecene, cyclopentadiene, cyclohexadiene, cyclooctadiene and cyclodecadiene;

polycyclic saturated hydrocarbons such as bicyclo[2.2.1]heptane, bicyclo[2.2.2]octane, tricyclo[5.2.1.0$^{2,6}$]decane, tricyclo[3.3.1.1$^{3,7}$]decane, tetracyclo[6.2.1.1$^{3,6}$.0$^{2,7}$]dodecane and adamantane;

polycyclic hydrocarbon groups such as bicyclo[2.2.1]heptene, bicyclo[2.2.2]octene, tricyclo[5.2.1.0$^{2,6}$]decene, tricyclo[3.3.1.1$^{3,7}$]decene and tetracyclo[6.2.1.1$^{3,6}$.0$^{2,7}$]dodecene.

Examples of the aromatic hydrocarbon group having 6 to 30 carbon atoms include groups derived from any of aromatic hydrocarbons such as benzene, naphthalene, phenanthrene, anthracene, tetracene, pentacene, pyrene, picene, toluene, xylene, ethylbenzene, mesitylene and cumene by removing (k+1) hydrogen atoms therefrom.

In the above formula (8), the divalent linking group having a fluorine atom represented by $X^c$ is exemplified by a divalent linear hydrocarbon group having 1 to 20 carbon atoms and having a fluorine atom. $X^c$ is exemplified by structures represented by the following formulae ($X^c$-1) to ($X^c$-6), and the like.

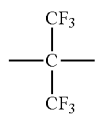

($X^c$-1)

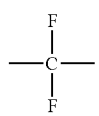

($X^c$-2)

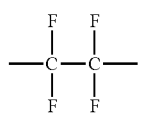

($X^c$-3)

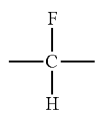

($X^c$-4)

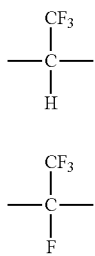
(X$^c$-5)

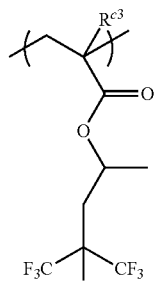
(X$^c$-6)

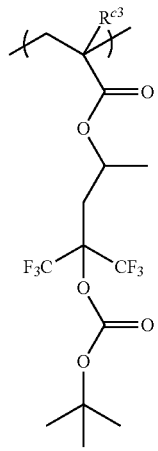
(8-1-1)

X$^c$ preferably represents a structure represented by the above formulae (X$^c$-1) and (X$^c$-2).

The organic group represented by R$^{20}$ in the above formula (5) is exemplified by a linear or branched hydrocarbon group having 1 to 30 carbon atoms, an alicyclic hydrocarbon group having 3 to 30 carbon atoms, an aromatic hydrocarbon group having 6 to 30 carbon atoms, or a group derived by combining such a group with an oxygen atom, a sulfur atom, an ether group, an ester group, a carbonyl group, an imino group, an amide group or a combination thereof.

Examples of the structural unit (c2) include structural units represented by the following formulae (8-1) and (8-2), and the like.

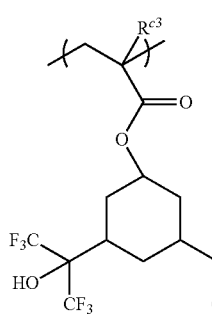
(8-1)

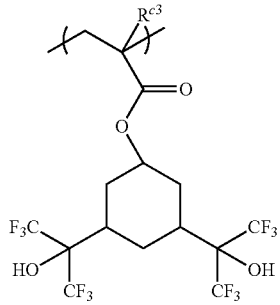
(8-1-2)

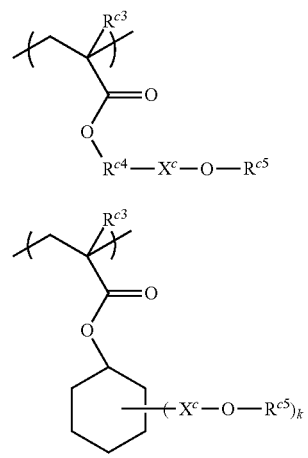
(8-2)

(8-2-1)

In the above formula (8-1), R$^{c4}$ represents a divalent hydrocarbon group having 1 to 20 carbon atoms; R$^{c3}$, X$^c$ and R$^{c5}$ are as defined in the above formula (8).

In the formula (8-2), R$^{c3}$, X$^c$, R$^{c5}$ and k are as defined in the above formula (8), wherein in a case where k is 2 or 3, a plurality of X$^c$s are each identical or different and a plurality of R$^{c5}$ are each identical or different.

The structural units represented by the above formula (8-1) and formula (8-2) are exemplified by structural units represented by the following formula (8-1-1), formula (8-1-2) and formula (8-2-1), and the like.

In the above formulae (8-1-1), (8-1-2) and (8-2-1), R$^{c3}$ is as defined in the above formula (8).

Examples of the monomer that gives the structural unit (c2) include (meth)acrylic acid (1,1,1-trifluoro-2-trifluoromethyl-2-hydroxy-3-propyl) ester, (meth)acrylic acid (1,1,1-trifluoro-2-trifluoromethyl-2-hydroxy-4-butyl) ester, (meth)acrylic acid (1,1,1-trifluoro-2-trifluoromethyl-2-hydroxy-5-pentyl) ester, (meth)acrylic acid (1,1,1-trifluoro-2-trifluoromethyl-2-hydroxy-4-pentyl) ester, (meth)acrylic acid 2-{[5-(1',1',1'-trifluoro-2'-trifluoromethyl-2'-hydroxy)propyl]bicyclo[2.2.1]heptyl}ester, and the like.

The content of the structural unit (c2) in the polymer (C) is preferably 20 mol % to 80 mol %, and more preferably 30 mol % to 70 mol %. It is to be noted that the polymer (C) may include one, or two or more types of the structural unit (c2).

Other Structural Unit

The polymer (C) may further include as "other structural unit", one or more of a structural unit having a lactone structure or a cyclic carbonate structure in order to increase solubility in a developer solution, a structural unit having an alicyclic structure in order to etching resistance in order to increase solubility in a developer solution, and the like. The structural unit having a lactone structure or a cyclic carbonate structure and the structural unit having an alicyclic structure are exemplified by structural units similar to those exemplified as the structural unit (b2) having a lactone structure or a cyclic carbonate structure of the polymer (B).

The content of the other structural unit in the polymer (C) is typically no greater than 90 mol %, preferably 10 mol % to 80 mol %, and more preferably 20 mol % to 70 mol %. It is to be noted that the polymer (C) may include one, or two or more types of the other structural unit.

The amount of the polymer (C) blended with respect to 100 parts by mass of the polymer (B) is preferably 0.1 part by mass to 20 parts by mass, more preferably 1 part by mass to 10 parts by mass, and still more preferably 1 part by mass to 7.5 parts by mass. When the amount is less than 0.1 parts by mass, the effects achievable by containing the polymer (C) may not be sufficient. On the other hand, when the amount exceeds 20 parts by mass, water repellency of the surface of the resist significantly increases so that poor development may occur.

The content of the fluorine atoms in the polymer (C) is preferably greater than that of the polymer (B). The content of the fluorine atoms in the polymer (C) with respect to 100% by mass of the total amount of the polymer (C) is typically no less than 5% by mass, preferably 5% by mass to 50% by mass, and more preferably 5% by mass to 45% by mass. It is to be noted that the content of the fluorine atoms may be determined by $^{13}$C-NMR. When the content of fluorine atoms in the polymer (C) is greater than that of the polymer (B), water repellency of the surface of the photoresist film formed from the radiation-sensitive resin composition containing the polymer (C) and the polymer (B) described above can be improved, and thus necessity of separately forming an upper layer film in liquid immersion lithography can be obviated. In order to sufficiently achieve the effect described above, the difference between the content of the fluorine atoms in the polymer (B) and the content of fluorine atom in the polymer (C) is preferably no less than 1% by mass, and more preferably no less than 3% by mass.

Synthesis Method of Polymer (C)

The polymer (C) may be produced by, for example, polymerizing a monomer corresponding to each predetermined structural unit using a radical polymerization initiator in an appropriate solvent.

Examples of the radical polymerization initiator and the solvent for use in the polymerization include those exemplified in the synthesis method of the polymer (B).

The reaction temperature in the polymerization is typically 40° C. to 150° C., and preferably 50° C. to 120° C. The reaction time period is typically 1 hr to 48 hrs, and preferably 1 hr to 24 hrs.

Mw of the polymer (C) is preferably 1,000 to 50,000, more preferably 1,000 to 40,000, and particularly preferably 1,000 to 30,000. When the Mw of the polymer (C) is less than 1,000, attaining a satisfactory receding contact angle may fail. To the contrary, when the Mw of the polymer (C) exceeds 50,000, developability when a resist is provided tends to be inferior.

The ratio (Mw/Mn) of Mw to polystyrene equivalent number average molecular weight (Mn) as determined by a GPC method of the polymer (C) is preferably 1 to 5, and more preferably 1 to 4.

Nitrogen-Containing Compound (D)

The nitrogen-containing compound (D) has an effect of controlling a phenomenon of diffusion of an acid, which is generated from the compound (A) and/or the other acid generating upon exposure, in the resist coating film, and inhibiting an undesired chemical reaction in an unexposed region. Thus, resolution as a resist is further improved, and storage stability of the resulting radiation-sensitive resin composition is improved. The mode of incorporation of the nitrogen-containing compound (D) into the radiation-sensitive resin composition may be in a free compound form or in an incorporated form as a part of the polymer, or in both of these forms.

Examples of the nitrogen-containing compound (D) include compounds represented by the following formula, and the like.

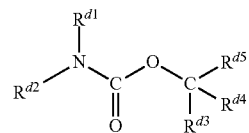

In the above formula, $R^{d1}$ to $R^{d5}$ each independently represent a hydrogen atom, or a hydrocarbon group having 1 to 20 carbon atoms, wherein these groups do not have or have a substituent, and wherein $R^{d1}$ and $R^{d2}$ may taken together represent a saturated or unsaturated divalent hydrocarbon group having 4 to 20 carbon atoms or a derivative thereof together with the nitrogen atom to which $R^{d1}$ and $R^{d2}$ bond, and/or $R^{d3}$ and $R^{d4}$ may taken together represent a saturated or unsaturated divalent hydrocarbon group having 4 to 20 carbon atoms or a derivative thereof together with the carbon atom to which $R^{d3}$ and $R^{d4}$ bond.

Examples of the nitrogen-containing compound (D) represented by the above formula include N-t-alkylalkoxycarbonyl group-containing amino compounds such as N-t-butoxycarbonyl di-n-octylamine, N-t-amyloxycarbonyl di-n-octylamine, N-t-butoxycarbonyl di-n-nonylamine, N-t-amyloxycarbonyl di-n-nonylamine, N-t-butoxycarbonyl di-n-decylamine, N-t-amyloxycarbonyl di-n-decylamine, N-t-butoxycarbonyl dicyclohexylamine, N-t-amyloxycarbonyl dicyclohexylamine, N-t-butoxycarbonyl-1-adamantylamine, N-t-amyloxycarbonyl-1-adamantylamine, N-t-butoxycarbonyl-2-adamantylamine, N-t-amyloxycarbonyl-2-adamantylamine, N-t-butoxycarbonyl-N-methyl-1-adamantylamine, N-t-amyloxycarbonyl-N-methyl-1-adamantylamine, (S)-(−)-1-(t-butoxycarbonyl)-2-pyrrolidinemethanol, (S)-(−)-1-(t-amyloxycarbonyl)-2-pyrrolidinemethanol, (R)-(+)-1-(t-butoxycarbonyl)-2-pyrrolidinemethanol, (R)-(+)-1-(t-amyloxycarbonyl)-2-pyrrolidinemethanol, N-t-butoxycarbonyl-4-hydroxypiperidine, N-t-amyloxycarbonyl-4-hydroxypiperidine, N-t-butoxycarbonylpyrrolidine, N-t-amyloxycarbonylpyrrolidine, N,N'-di-t-butoxycarbonylpiperazin, N,N'-di-t-amyloxycarbonylpiperazine, N,N-di-t-butoxycarbonyl-1-adamantylamine, N,N-di-t-amyloxycarbonyl-1-adamantylamine, N-t-butoxycarbonyl-4,4'-diaminodiphenylmethane, N-t-amyloxycarbonyl-4,4'-diaminodiphenylmethane, N,N'-di-t-butoxycarbonyl hexamethylenediamine, N,N'-di-t-amyloxycarbonyl hexamethylenediamine, N,N,N',N'-tetra-t-butoxycarbonyl hexamethylenediamine, N,N,N',N'-tetra-t-amyloxycarbonyl hexamethylenediamine, N,N'-di-t-butoxycarbonyl-1,7-diaminoheptane, N,N'-di-t-amyloxycarbonyl-1,7-diaminoheptane, N,N'-di-t-butoxycarbonyl-1,8-diaminooctane, N,N'-di-t-amyloxycarbonyl-1,8-diaminooctane, N,N'-di-t-butoxycarbonyl-1,9-diaminononane, N,N'-di-t-amyloxycarbonyl-1,9- diaminononane, N,N'-di-t-butoxycarbonyl-1,10-diaminodecane, N,N'-di-t-amyloxycarbonyl-1,10-diaminodecane, N,N'-di-t-butoxycarbonyl-1,12-diaminododecane, N,N'-di-t-amyloxycarbonyl-1,12-diaminododecane, N,N'-di-t-butoxycarbonyl-4,4'-diaminodiphenylmethane, N,N'-di-t-amyloxycarbonyl-4,4'-diaminodiphenylmethane, N-t-butoxycarbonylbenzimidazole, N-t-butoxycarbonylbenzimidazole, N-t-amyloxycarbonyl-2-methylbenzimidazole, N-t-butoxycarbonyl-2-phenylbenzimidazole and N-t-amyloxycarbonyl-2-phenylbenzimidazole, and the like.

Moreover, the nitrogen-containing compound is exemplified by a tertiary amine compound, a quaternary ammonium hydroxide compound, a photodegradable base compound, as well as other nitrogen-containing heterocycle compound and the like, in addition to the nitrogen-containing compound represented by the above formula.

Examples of the tertiary amine compound include:

tri(cyclo)alkylamines such as triethylamine, tri-n-propylamine, tri-n-butylamine, tri-n-pentylamine, tri-n-hexylamine, tri-n-heptylamine, tri-n-octylamine, cyclohexyl dimethylamine, dicyclohexylmethylamine and tricyclohexylamine;

aromatic amines such as aniline, N-methylaniline, N,N-dimethylaniline, 2-methylaniline, 3-methylaniline, 4-methylaniline, 4-nitroaniline, 2,6-dimethylaniline and 2,6-diisopropylaniline;

alkanolamines such as triethanolamine, N,N-di(hydroxyethyl)aniline;

N,N,N',N'-tetramethylethylenediamine, N,N,N',N'-tetrakis(2-hydroxypropyl)ethylenediamine, 1,3-bis[1-(4-aminophenyl)-1-methylethyl]benzenetetramethylenediamine, bis(2-dimethylaminoethyl)ether, bis(2-diethylaminoethyl) ether, and the like.

Examples of the quaternary ammonium hydroxide compound include tetra-n-propylammonium hydroxide, tetra-n-butylammonium hydroxide, and the like.

The amount of the nitrogen-containing compound (D) used is preferably no greater than 10 parts by mass, and more preferably no greater than 8 parts by mass with respect to 100 parts by mass of the polymer (B). When the amount used exceeds 10 parts by mass, sensitivity as a resist is likely to be decreased.

Solvent (E)

The radiation-sensitive resin composition usually contains the solvent (E). The solvent (E) is exemplified by an alcohol solvent, a ketone solvent, an amide solvent, an ether solvent, an ester solvent and a mixed solvent thereof, and the like. In the radiation-sensitive resin composition, one, or two or more types of the solvent (E) may be used.

Examples of the alcohol solvent include:

monoalcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethyl nonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

partially etherified polyhydric alcohol solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether, and the like.

Examples of the ketone solvent include ketone solvents such as acetone, methyl ethyl ketone, methyl-n-propyl ketone, methyl-n-butyl ketone, diethyl ketone, methyl-iso-butyl ketone, methyl-n-pentyl ketone, ethyl-n-butyl ketone, methyl-n-hexyl ketone, di-iso-butyl ketone, trimethyl nonanone, cyclopentanone, cyclohexanone, cycloheptanone, cyclooctanone, methylcyclohexanone, 2,4-pentanedione, acetonyl acetone, diacetonealcohol, acetophenone, and the like.

Examples of the amide solvent include N,N'-dimethylimidazolidinone, N-methylformamide, N,N-dimethylformamide, N,N-diethylformamide, acetamide, N-methylacetamide, N,N-dimethylacetamide, N-methylpropionamide, N-methylpyrrolidone, and the like.

Examples of the ester solvent include diethyl carbonate, propylene carbonate, methyl acetate, ethyl acetate, γ-butyrolactone, γ-valerolactone, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, diglycol acetate, methoxytriglycol acetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of the other solvent include:

aliphatic hydrocarbon solvents such as n-pentane, iso-pentane, n-hexane, iso-hexane, n-heptane, iso-heptane, 2,2,4-trimethyl pentane, n-octane, iso-octane, cyclohexane and methylcyclohexane;

aromatic hydrocarbon solvents such as benzene, toluene, xylene, mesitylene, ethylbenzene, trimethyl benzene, methylethylbenzene, n-propylbenzene, iso-propylbenzene, diethylbenzene, iso-butylbenzene, triethylbenzene, di-iso-propylbenzene and n-amylnaphthalene;

halogen-containing solvents such as dichloromethane, chloroform, chlorofluorocarbon, chlorobenzene and dichlorobenzene, and the like.

Among these solvents, propylene glycol monomethyl ether acetate, propylene glycol monomethyl ether, ethyl lactate, γ-butyrolactone, and cyclohexanone are preferred.

Other Optional Components

The radiation-sensitive resin composition may contain (F) an uneven distribution accelerator, an alicyclic skeleton compound, a surfactant, a sensitizing agent and the like, within a range not leading to impairment of the effects of the embodiment of the present invention. These other optional components will be described in detail below. These other optional components may be used either alone, or as a mixture of two or more types thereof. Also, the amount of the other optional component blended may be predetermined ad libitum in accordance with the object thereof.

Uneven Distribution Accelerator (F)

The radiation-sensitive resin composition can be blended with the uneven distribution accelerator (F) in such a case where a resist pattern is formed using a liquid immersion lithography process. Blending the uneven distribution accelerator (F) enables the polymer (C) to be unevenly distributed in further vicinity of the surface of the layer. Examples of the uneven distribution accelerator (F) include γ-butyrolactone, propylenecarbonate, and the like.

Alicyclic Skeleton Compound

The alicyclic skeleton compound is a component that exhibits actions of further improving the dry etching resistance, pattern configuration, adhesiveness to a substrate, and the like.

Surfactant

The surfactant is a component that exhibits actions of improving coating properties, striation, developability, and the like.

Sensitizing Agent

The sensitizing agent serves in absorbing the energy of radioactive rays, and transferring the energy to the compound (A), thereby increasing the amount of acid generation, and thus has an effect of improving "apparent sensitivity" of the radiation-sensitive resin composition.

Preparation of Radiation-sensitive Composition

The radiation-sensitive resin composition may be prepared by, for example, mixing the compound (A), the polymer (B), the polymer (C) which is added as needed, and the other optional components at a certain ratio in the solvent (E). An organic solvent is not particularly limited as long as it is exemplified as the solvent (E) and is capable of dissolving or dispersing the compound (A), the polymer (B), the polymer (C), and the other optional component. The radiation-sensitive resin composition is prepared generally by dissolving such that t total solid content concentration becomes 1% by mass to 50% by mass, and preferably 2% by mass to 25% by mass in the solvent (E) upon use thereof, and thereafter filtering through a filter having a pore size of about 0.2 μm, for example.

Pattern-Forming Method

The pattern-forming method in which the radiation-sensitive resin composition of the embodiment of the present invention is used is exemplified by a method including the steps of, for example:

providing a resist film on a substrate using the radiation-sensitive resin composition (hereinafter, may be also referred to as "step (i)");

exposing the resist film (hereinafter, may be also referred to as "step (ii)"); and developing the exposed resist film with an alkali (hereinafter, may be also referred to as "step (iii)"), and the like. Each step will be described in detail below.

Step (i)

In this step, the radiation-sensitive resin composition or a composition solution prepared by: dissolving the same in a solvent is coated on a substrate such as a silicon wafer, silicon dioxide or a wafer covered with an underlayer antireflective film by a coating means such as spin-coating, cast coating or roll coating so as to give a predetermined film thickness; and then prebaking to volatilize the solvent in the coated film, thereby forming a resist film. It is to be noted that the underlayer antireflective film may be formed on the surface of the substrate using, for example, underlayer antireflective film-forming agent.

Step (ii)

In this step, the resist film formed in the step (i) is exposed by irradiating with a radioactive ray (through a medium for liquid immersion such as water as the case may be). It is to be noted that the radioactive ray is irradiated through a mask having a certain pattern in this step. The radioactive ray is appropriately selected from visible light rays, ultraviolet rays, far ultraviolet rays, X-rays, charged particle rays and the like in accordance with the line width of an intended pattern, and then irradiated. The radioactive ray is preferably a far ultraviolet ray typified by an ArF excimer laser (wavelength: 193 nm) or a KrF excimer laser (wavelength: 248 nm), and more preferably an ArF excimer laser (wavelength: 193 nm). Next, the exposed photoresist film is subjected to post exposure baking (PEB), thereby deprotecting the polymer at the exposed site of the resist film due to the acid generated from the compound (A). PEB is carried out by appropriately selecting the temperature typically within the range of 50° C. to 180° C.

Step (iii)

In this step, a predetermined photoresist pattern is formed by subjecting the exposed resist film to development by a developer solution. After the development, the film is generally washed with water and dried. Examples of the developer solution include aqueous alkali solutions prepared by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene or 1,5-diazabicyclo-[4.3.0]-5-nonene.

Moreover, when liquid immersion lithography is carried out, a protective film for liquid immersion that is soluble in a liquid immersion liquid may be also provided on the resist film before the step (ii) in order to prevent direct contact of the liquid immersion liquid with the resist film. As the protective film for liquid immersion, any of a solvent-peelable protective film which is peeled by a solvent before the step (iii) (for example, see Japanese Unexamined Patent Application, Publication No. 2006-227632), a developer solution-peelable protective film which is peeled concomitant with the development in the step (ii) (for example, see WO 2005-069076 and WO 2006-035790) may be used. However, in light of the throughput, developer solution-peelable protective film for liquid immersion is preferably used.

According to the resist pattern-forming method in which the radiation-sensitive resin composition of the embodiment of the present invention is used, a fine pattern that is superior in pattern configuration can be formed; therefore, the method is suited for microfabrication in which a lithography technique is applied.

Compound

The compound of the embodiment of the present invention is represented by the above formula (1). The compound is preferably represented by the above formula (2) among its candidates represented by the above formula (1). Additionally, compounds represented by the above formulae (1) and (2) are preferred, wherein $R^1$ represents —$OR^5$; and $R^4$ represents —OR⁶, wherein $R^5$ and $R^6$ each independently represent an alkyl group having 1 to 10 carbon atoms, an alicyclic group having 3 to 10 carbon atoms or a group having a lactone structure having 4 to 12 carbon atoms. The compound can be suitably used as an acid generating agent contained in a radiation-sensitive resin composition for forming a resist film, and the like. With respect to detailed description of the compound, description of the compound (A) contained in the radiation-sensitive resin composition may be applicable.

The embodiment of the present invention also involves the compound represented by the above formula (3). The compound is used for synthesis of the compound represented by the above formula (1). As a synthesis method of the compound represented by the above formula (1) in which the compound is used, a method similar to that described in the explanation in connection with the compound (A) contained in the radiation-sensitive resin composition may be employed. In addition, the compound represented by the above formula (3) is exemplified by compounds similar to those exemplified as the intermediate compound (*-3) of the synthesis in the explanation in connection with the synthesis method of the compound (A).

EXAMPLES

Hereinafter, the present invention will be explained more specifically by way of Examples, but the present invention is not limited to these Examples.

The Mw and the Mn of the polymer were determined using GPC columns (Tosoh Corporation, "G2000HXL"×2, "G3000HXL"×1, and "G4000HXL"×1) under the following conditions.

column temperature: 40° C.
elution solvent: tetrahydrofuran (Wako Pure Chemical Industries, Ltd.)
flow rate: 1.0 mL/min
sample concentration: 1.0% by mass
amount of the sample injected: 100 μL
detector: differential refractometer
standard substance: monodisperse polystyrene The $^{19}$F-NMR analysis and the $^{13}$C-NMR analysis were conducted using a nuclear magnetic resonance apparatus (JEOL, Ltd., JNM-GX400) for the measurement.

Synthesis of Intermediate Compound

Example 1

Into an autoclave were charged 108.5 g of dicyclopentadiene and 322.4 g of 1-bromo-1,1,2,2-tetrafluoro-3-butene, and a solution prepared by dissolving 0.3 g of 4-methoxyphenol in 5 mL of toluene was added thereto as a polymerization inhibitor. After stirring at 170° C. for 5 hrs, the mixture was subjected to distillation in vacuo at 85° C. and 25 mmHg to perform purification. Thus, 326 g of colorless liquid 1-bromo-1,1,2,2-tetrafluoro-2-(norbor-5-en-2-yl)ethane (intermediate compound (a-1)) represented by the following formula (a-1) was obtained.

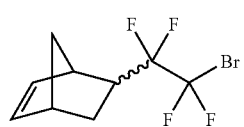

(a-1)

$^{19}$F-NMR (CDCl₃) δ (ppm): −62.56 to −64.24 (m), −107.02 (d), −108.80 (d), −111.56 (d), −112.56 (d)

Synthesis of Compound (A)

Example 2

Synthesis of Compound (A-1)

Synthesis of Precursor Compound (a-2)

Into a glass flask equipped with a thermometer and a capacitor were charged 15.0 g (54.9 mmol) of the intermediate compound (a-1) obtained in Example 1, 165 g of water, 110 g of acetonitrile, 110 g of ethyl acetate and 228 mg (1.10 mmol) of ruthenium trichloride, and the mixture was stirred on an ice bath for 15 min. Thereafter, 48.2 g (225 mmol) of sodium periodate was charged thereto with an attention such that the temperature in the system does not exceed 20° C., and then the mixture was further stirred for 30 min. Thereafter, the reaction was further allowed at room temperature for 2 hrs, and the disappearance of the raw material was confirmed by TLC to decide completion of the reaction.

After the completion of the reaction, the precipitated salt was removed by filtration, and the filtrate was extracted with 150 mL of ethyl acetate twice. Thereafter, the organic layer was washed with 100 mL of 0.5 M hydrochloric acid six times, and then with 100 mL of saturated brine once. Distillation of the solvent gave 17.9 g of 4-(2-bromo-1,1,2,2-tetrafluoroethyl)cyclopentane-1,3-dicarboxylic acid (precursor compound (a-2)) represented by the following formula (a-2) (yield: 97%).

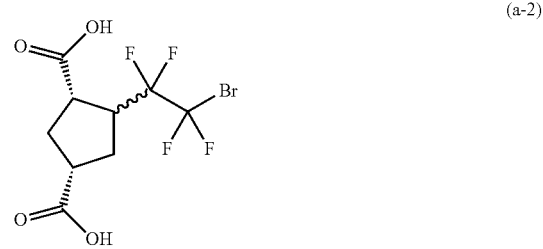 [SMILES: O=C(O)[C@H]1CC(C(F)(F)C(F)(F)Br)[C@@H](C(=O)O)C1]

(a-2)

$^{19}$F-NMR (CDCl₃) δ (ppm): −63.18, −63.57, −106.67, −109.71, −114.41, −116.39

Synthesis of Precursor Compound (a-3)

Into a glass flask were charged 3.00 g (8.90 mmol) of 4-(2-bromo-1,1,2,2-tetrafluoroethyl)cyclopentane-1,3-dicarboxylic acid, 50 g of methanol and 0.300 g of p-toluenesulfonic acid, and the mixture was refluxed using a Dean and Stark apparatus for 10 hrs. Thereafter, the solvent was distilled off, and 100 mL of ethyl acetate was added thereto. The organic layer was washed with 50 mL of an aqueous sodium bicarbonate solution three times, and then with 50 mL of saturated brine once. After washing, the solvent of the organic layer was distilled off, and purification was carried out on column chromatography to obtain 2.05 g of dimethyl 4-(2-bromo-1,1,2,2-tetrafluoroethyl)cyclopentane-1,3-dicarboxylate (precursor compound (a-3)) represented by the following formula (a-3) (yield: 63%).

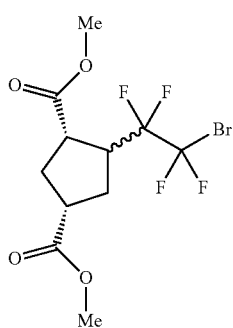

(a-3)

$^{19}$F-NMR (CDCl$_3$) δ (ppm): −63.41 to −63.58 (m), −107.23 (d), −110.04 (d), −115.33 (d), −116.41 (d)

Synthesis of Precursor Compound (a-4)

Into a glass flask equipped with a thermometer and a capacitor were charged 2.00 g (5.49 mmol) of dimethyl 4-(2-bromo-1,1,2,2-tetrafluoroethyl)cyclopentane-1,3-dicarboxylate, 0.920 g (11.0 mmol) of sodium bicarbonate, 1.62 g (9.30 mmol) of sodium dithionite, 15 mL of acetonitrile and 15 mL of water, and the mixture was stirred at 50° C. for 8 hrs. The disappearance of the raw material was confirmed by $^{19}$F-NMR to decide completion of the reaction. Thereafter, acetonitrile was distilled off in vacuo to obtain an aqueous solution of crude sodium 2-(2,4-bis(methoxycarbonyl)cyclopentyl)-1,1,2,2-tetrafluoroethanesulfinate (precursor compound (a-4)) represented by the following formula (a-4) without carrying out further purification, which was used for the following reaction.

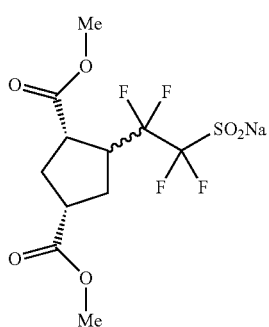

(a-4)

Synthesis of Precursor Compound (a-5)

Into a glass flask equipped with a thermometer and a capacitor were charged the aqueous solution of crude sodium 2-(2,4-bis(methoxycarbonyl)cyclopentyl)-1,1,2,2-tetrafluoroethanesulfinate obtained as described above, and a catalytic amount of sodium tungstate (IV) dihydrate. Thereto, a 35% by mass hydrogen peroxide solution 3.00 g was added dropwise. After the mixture was stirred at room temperature for 5 hrs, the disappearance of the raw material was confirmed by $^{19}$F-NMR to decide completion of the reaction. After the completion of the reaction, 20 mL of water was further added thereto, and the aqueous layer was washed with 30 mL of dichloromethane five times to obtain an aqueous solution of sodium 2-(2,4-bis(methoxycarbonyl)cyclopentyl)-1,1,2,2-tetrafluoroethanesulfonate (precursor compound (a-5)) represented by the following formula (a-5), which was used for the following reaction.

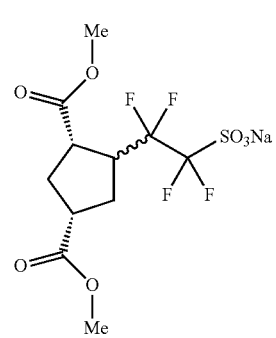

(a-5)

Into a glass flask equipped with a thermometer and a capacitor were charged the aqueous solution of sodium 2-(2,4-bis(methoxycarbonyl)cyclopentyl)-1,1,2,2-tetrafluoroethanesulfonate obtained as described above, and 1.31 g (4.38 mmol) of triphenylsulfonium chloride, and the mixture was stirred at room temperature for 6 hrs. Thereafter, the reaction liquid was extracted with 30 mL of dichloromethane three times, and the resultant organic layer was washed with 100 mL of water six times. Distillation of dichloromethane in vacuo gave 1.51 g of triphenylsulfonium 2-(2,4-bis(methoxycarbonyl)cyclopentyl)-1,1,2,2-tetrafluoroethanesulfonate (compound (A-1)) represented by the following formula (A-1).

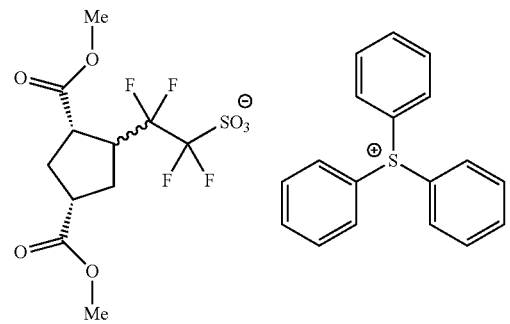

(A-1)

$^{19}$F-NMR (CDCl$_3$) δ (ppm): −108.98, −109.16, −109.72, −109.85, −112.80, −113.49, −114.03, −114.70, −115.21, −115.90, −117.37, −117.85, −118.07, −118.47, −120.46, −120.78

Example 3

Synthesis of Compound (A-2)

Into a glass flask were charged 3.00 g (8.90 mmol) of 4-(2-bromo-1,1,2,2-tetrafluoroethyl)cyclopentane-1,3-dicarboxylic acid, 25 g of isopropanol, 25 g of cyclohexane and 0.300 g of p-toluenesulfonic acid, and the mixture was refluxed using a Dean and Stark apparatus for 10 hrs. Thereafter, the solvent was distilled off, and 100 mL of ethyl acetate was added thereto. The organic layer was washed with 50 mL of an aqueous sodium bicarbonate solution three times, and then with 50 mL of saturated brine once. After washing, the solvent of the organic layer was distilled off, and purification was carried out on column chromatography to obtain 1.54 g of diisopropyl 4-(2-bromo-1,1,2,2-tetrafluoroethyl)cyclopentane-1,3-dicarboxylate (precursor compound (a-6)) represented by the following formula (a-6) (yield: 41%).

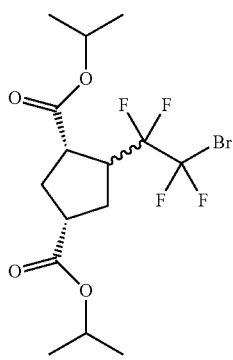

(a-6)

Triphenylsulfonium 2-(2,4-bis(isopropoxycarbonyl)cyclopentyl)-1,1,2,2-tetrafluoroethanesulfonate represented by the following formula (A-2) (compound (A-2)) was obtained in a similar manner to the synthesis method of (A-1) except that diisopropyl 4-(2-bromo-1,1,2,2-tetrafluoroethyl)cyclopentane-1,3-dicarboxylate was used in place of dimethyl 4-(2-bromo-1,1,2,2-tetrafluoroethyl)cyclopentane-1,3-dicarboxylate.

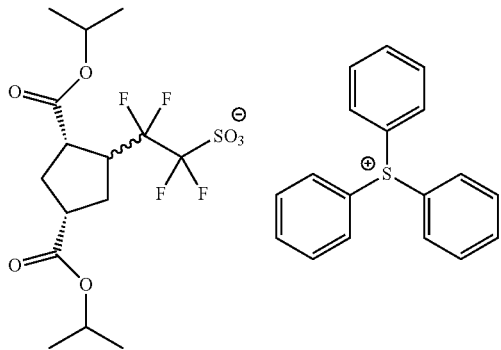

(A-2)

Example 4

Synthesis of Compound (A-3)

Synthesis of Precursor Compound (a-7)

Into a glass flask were charged 3.00 g (8.90 mmol) of 4-(2-bromo-1,1,2,2-tetrafluoroethyl)cyclopentane-1,3-dicarboxylic acid, 13.7 g (89.0 mmol) of 4-oxa-5-oxotricyclo[4.2.1.0$^{3,7}$]nonan-2-ol, 50 g of toluene and 0.300 g of p-toluenesulfonic acid, and the mixture was refluxed using a Dean and Stark apparatus for 26 hrs. Thereafter, the solvent was distilled off, and 100 mL of dichloromethane was added thereto. The organic layer was washed with 50 mL of an aqueous sodium bicarbonate solution three times, with 50 mL of water five times, and then 50 mL of saturated brine once. After washing, the solvent of the organic layer was distilled off, and purification was carried out on column chromatography to obtain 2.33 g of bis(4-oxa-5-oxotricyclo[4.2.1.0$^{3,7}$]nonan-2-yl)-4-(2-bromo-1,1,2,2-tetrafluoroethyl)cyclopentane-1,3-dicarboxylate (precursor compound (a-7)) represented by the following formula (a-7) (yield: 43%).

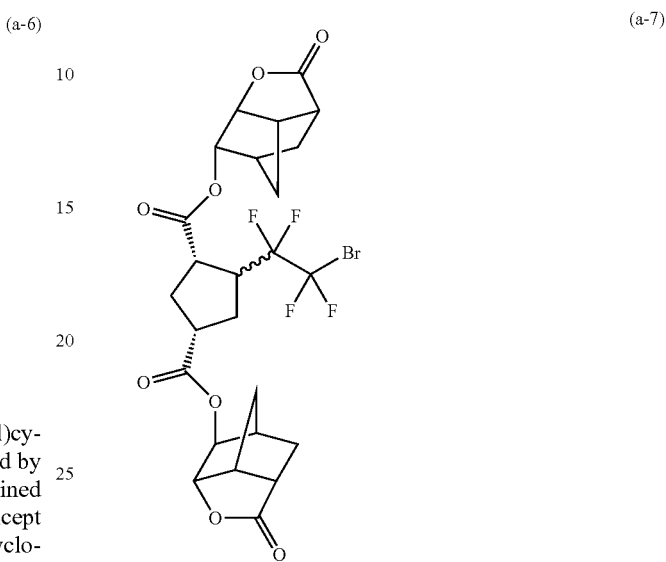

(a-7)

Triphenylsulfonium 2-(2,4-bis(4-oxa-5-oxotricyclo[4.2.1.0$^{3,7}$]nonan-2-yloxy)cyclopentyl)-1,1,2,2-tetrafluoroethanesulfonate (compound (A-3)) represented by the following formula (A-3) was obtained in a similar manner to the synthesis method of (A-1) except that bis(4-oxa-5-oxotricyclo[4.2.1.0$^{3,7}$]nonan-2-yl)-4-(2-bromo-1,1,2,2-tetrafluoroethyl)cyclopentane-1,3-dicarboxylate was used in place of dimethyl 4-(2-bromo-1,1,2,2-tetrafluoroethyl)cyclopentane-1,3-dicarboxylate.

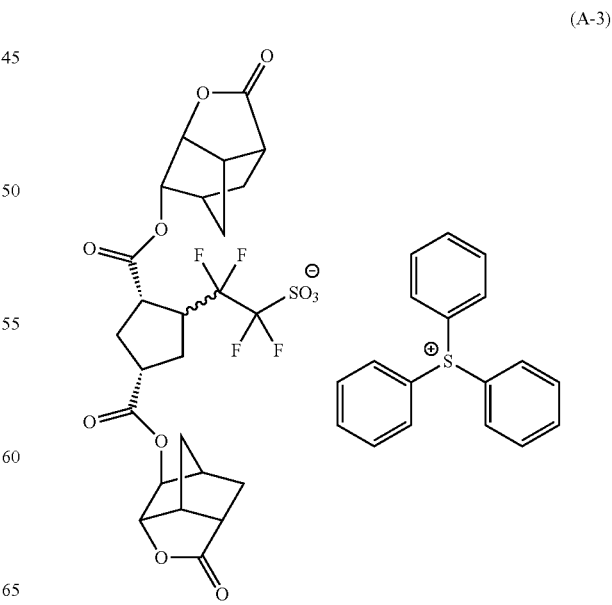

(A-3)

$^{19}$F-NMR (CDCl$_3$) δ (ppm): −108.01 to −109.89 (m), −113.15 to −114.31 (m), −116.51 to −118.23 (m), −120.72 to −122.80 (m)

Example 5

Synthesis of Compound (A-4)

Synthesis of Precursor Compound (a-8)

Into a glass flask were charged 3.00 g (8.90 mmol) of 4-(2-bromo-1,1,2,2-tetrafluoroethyl)cyclopentane-1,3-dicarboxylic acid, 8.83 g (89.0 mmol) of cyclohexylamine and 50 g of toluene, and the mixture was refluxed using a Dean and Stark apparatus for 10 hrs. Thereafter, the solvent was distilled off, and 100 mL of dichloromethane was added thereto. The organic layer washed with 50 mL of 1 M aqueous hydrochloric acid four times, with 50 mL of an aqueous sodium bicarbonate solution three times, and then with 50 mL of saturated brine once. After washing, the solvent of the organic layer was distilled off, and purification was carried out on column chromatography to obtain 3.38 g of 4-(2-bromo-1,1,2,2-tetrafluoroethyl)-N$^1$,N$^3$-dicyclohexylcyclopentane-1,3-dicarboxamide (precursor compound (a-8)) represented by the following formula (a-8) (yield: 76%).

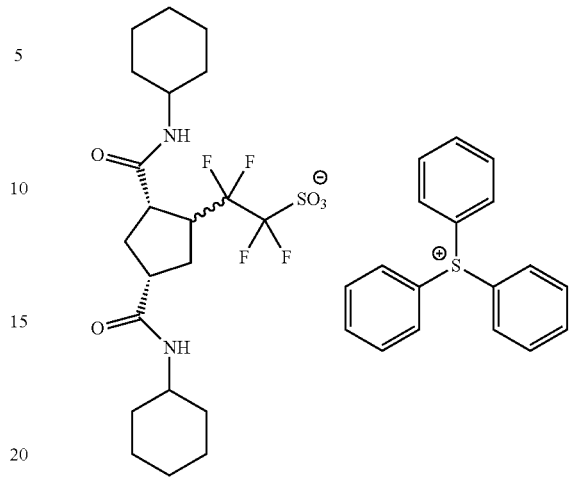

(a-8)

Triphenylsulfonium 2-(2,4-bis(cyclohexyl carbamoyl)cyclopentyl)-1,1,2,2-tetrafluoroethanesulfonate (compound (A-4)) represented by the following formula (A-4) was obtained in a similar manner to the synthesis method of (A-1) except that 4-(2-bromo-1,1,2,2-tetrafluoroethyl)-N$^1$,N$^3$-dicyclohexylcyclopentane-1,3-dicarboxamide was used in place of dimethyl 4-(2-bromo-1,1,2,2-tetrafluoroethyl)cyclopentane-1,3-dicarboxylate.

(A-4)

(A'-1) and (A'-2) used in Examples and Comparative Examples as the other acid generating agent are represented by the following formulae, respectively.

(A'-1): compound represented by the following formula (A'-1):

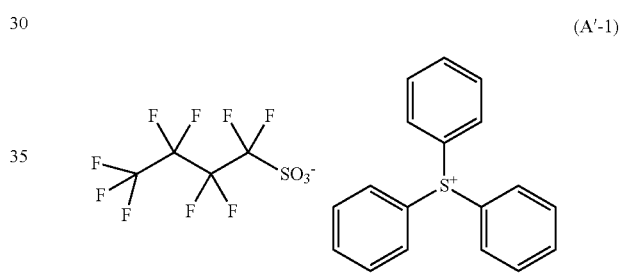

(A'-1)

(A'-2): compound represented by the following formula (A'-2):

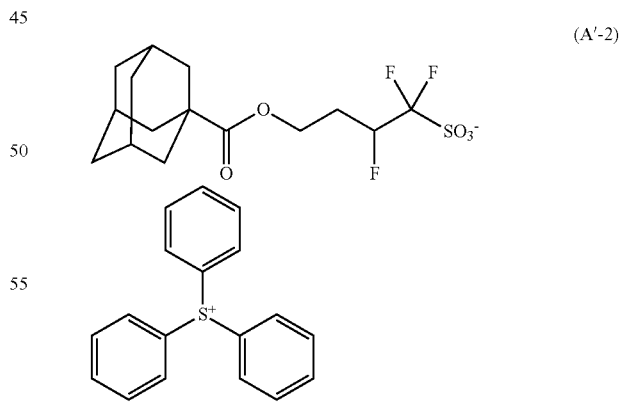

(A'-2)

Synthesis of Polymer (B)

Monomers used for the synthesis of the polymer (B), polymer (C) described later and polymers for an upper layer film are shown below.

(M-1) 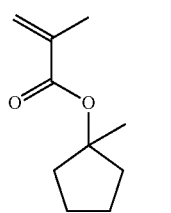
(M-2) 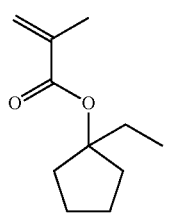
(M-3) 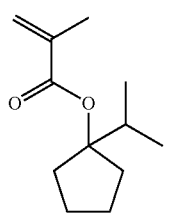
(M-4) 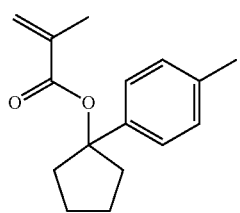
(M-5) 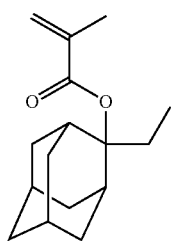
(M-6) 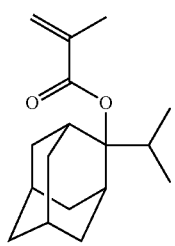
(M-7) 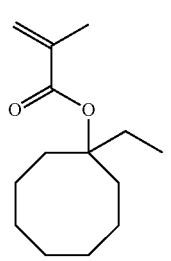
(M-8) 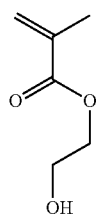
(M-9) 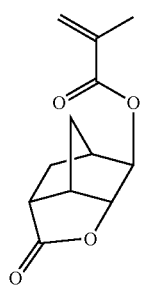
(M-10) 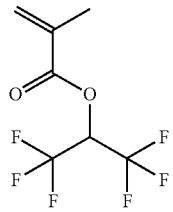
(M-11) 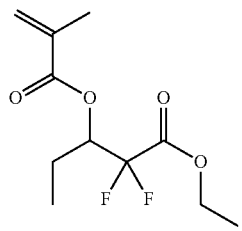
(M-12) 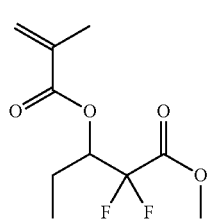
(M-13) 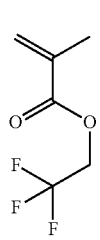

-continued

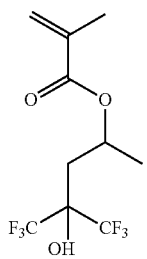
(M-14)

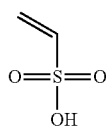
(M-15)

Synthesis Example 1

A monomer solution was prepared by dissolving 21.54 g (50 mol %) of the compound (M-1) and 28.46 g (50 mol %) of the compound (M-9) in 100 g of 2-butanone, and further charging thereto 2.13 g of azobisisobutyronitrile. After a 500 mL three-neck flask which had been charged with 50 g of 2-butanone was purged with nitrogen for 30 min, the reaction vessel was heated to 80° C. with stirring, and the monomer solution prepared as described above was added dropwise thereto over 3 hrs using a dropping funnel. A time point at which the dropwise addition was started was defined as a polymerization starting time, and the polymerization reaction was performed for 6 hrs.

After the completion of the polymerization, the polymerization solution was cooled to no higher than 30° C. by water-cooling, and charged into 1,000 g of methanol. The white powder thus precipitated was filtered off. The white powder obtained by filtration was dispersed into 200 g of methanol to give a slurry state, followed by washing and filtration. Such an operation was repeated twice, and then vacuum drying at 50° C. for 17 hrs gave a polymer (resin (B-1)) as a white powder (weight: 31 g; yield: 62%). The polymer had an Mw of 6,100, Mw/Mn of 1.4, and the content of fluorine atoms of 0.0%. As a result of the $^{13}$C-NMR analysis, the contents of (M-1) and (M-9) were 48 mol % and 52 mol %, respectively.

Synthesis Example 2

A monomer solution was prepared by dissolving 14.20 g (35 mol %) of the compound (M-1) and 26.81 g (50 mol %) of the compound (M-9) in 100 g of 2-butanone, and further charging thereto 1.98 g of azobisisobutyronitrile. After a 500 mL three-neck flask which had been charged with 50 g of 2-butanone and 8.99 g (15 mol %) of the compound (M-5) was purged with nitrogen for 30 min, the reaction vessel was heated to 80° C. with stirring, and the monomer solution prepared as described above was added dropwise thereto over 3 hrs using a dropping funnel. A time point at which the dropwise addition was started was defined as a polymerization starting time, and the polymerization reaction was performed for 6 hrs.

After the completion of the polymerization, the polymerization solution was cooled to no higher than 30° C. by water-cooling, and charged into 1,000 g of methanol. The white powder thus precipitated was filtered off. The white powder obtained by filtration was dispersed into 200 g of methanol to give a slurry state, followed by washing and filtration. Such an operation was repeated twice, and then vacuum drying at 50° C. for 17 hrs gave a polymer (resin (B-2)) as a white powder (weight: 35 g; yield: 70%). The polymer had an Mw of 6,300, Mw/Mn of 1.4, and the content of fluorine atoms of 0.0%. As a result of the $^{13}$C-NMR analysis, the contents of the structural units derived from (M-1), (M-5) and (M-9) were 34 mol %, 14 mol % and 52 mol %, respectively.

Synthesis Example 3

A monomer solution was prepared by dissolving 19.18 g (40 mol %) of the compound (M-3), 3.18 g (10 mol %) of the compound (M-8) and 24.43 g (45 mol %) of the compound (M-9) in 100 g of 2-butanone, and further charging thereto 2.00 g of azobisisobutyronitrile. After a 500 mL three-neck flask which had been charged with 50 g of 2-butanone and 3.21 g (5 mol %) of the compound (M-6) was purged with nitrogen for 30 min, the reaction vessel was heated to 80° C. with stirring, and the monomer solution prepared as described above was added dropwise thereto over 3 hrs using a dropping funnel. A time point at which the dropwise addition was started was defined as a polymerization starting time, and the polymerization reaction was performed for 6 hrs.

After the completion of the polymerization, the polymerization solution was cooled to no higher than 30° C. by water-cooling, and charged into 1,000 g of methanol. The white powder thus precipitated was filtered off. The white powder obtained by filtration was dispersed into 200 g of methanol to give a slurry state, followed by washing and filtration. Such an operation was repeated twice, and then vacuum drying at 50° C. for 17 hrs gave a polymer (resin (B-3)) as a white powder (weight: 37 g; yield: 74%). The polymer had an Mw of 6,100, Mw/Mn of 1.3, and the content of fluorine atoms of 0.0%. As a result of the $^{13}$C-NMR analysis, the contents of the structural units derived from (M-3), (M-6), (M-8) and (M-9) were 39 mol %, 5 mol %, 10 mol % and 46 mol %, respectively.

Synthesis of Polymer (C)

Synthesis Example 4

Synthesis of Polymer (C-1)

A monomer solution was prepared by dissolving 21.50 g (70 mol %) of the compound (M-2), 8.50 g (30 mol %) of the compound (M-13) and 60 g of 2-butanone, and further charging thereto 1.38 g of azobisisobutyronitrile. After a 300 mL three-neck flask which had been charged with 30 g of 2-butanone was purged with nitrogen for 30 min, the reaction vessel was heated to 80° C. with stirring, and the monomer solution prepared as described above was added dropwise thereto over 3 hrs using a dropping funnel. A time point at which the dropwise addition was started was defined as a polymerization starting time, and the polymerization reaction was performed for 6 hrs.

After the completion of the polymerization, the polymerization solution was cooled to no higher than 30° C. by water-cooling, and charged into 600 g of a solution containing methanol and water at a ratio of 8:2 to precipitate the resin. After removing the supernatant solution, 120 g of methanol was added to the precipitated resin to wash the resin. The supernatant liquid was removed, and thereafter the resin was dried at 50° C. for 17 hrs to obtain a polymer (C-1) of the compounds (M-2), and (M-13) (weight: 18 g; yield: 60%).

The polymer had an Mw of 5,800, Mw/Mn of 1.4, and the content of fluorine atoms of 9.6% by mass.

Synthesis Example 5

Synthesis of Polymer (C-2)

A monomer solution was prepared by dissolving 11.22 g (40 mol %) of the compound (M-7) and 18.78 g (60 mol %) of the compound (M-11) in 60 g of 2-butanone, and further charging thereto 1.03 g of azobisisobutyronitrile. After a 300 mL three-neck flask which had been charged with 30 g of 2-butanone was purged with nitrogen for 30 min, the reaction vessel was heated to 80° C. with stirring, and the monomer solution prepared as described above was added dropwise thereto over 3 hrs using a dropping funnel. A time point at which the dropwise addition was started was defined as a polymerization starting time, and the polymerization reaction was performed for 6 hrs.

After the completion of the polymerization, the polymerization solution was cooled to no higher than 30° C. by water-cooling, and charged into 600 g of a solution containing methanol and water at a ratio of 8:2 to precipitate the resin. After removing the supernatant solution, 120 g of methanol was added to the precipitated resin to wash the resin. The supernatant liquid was removed, and thereafter the resin was dried at 50° C. for 17 hrs to obtain a polymer (C-2) of the compounds (M-7), and (M-11) (weight: 19 g; yield: 62%). The polymer had an Mw of 5,700, Mw/Mn of 1.4, and the content of fluorine atoms of 9.5% by mass.

Synthesis Example 6

Synthesis of Polymer (C-3)

A monomer solution was prepared by dissolving 12.24 g (40 mol %) of the compound (M-4) and 17.76 g (60 mol %) of the compound (M-12) in 60 g of 2-butanone, and further charging thereto 1.03 g of azobisisobutyronitrile. After a 300 mL three-neck flask which had been charged with 30 g of 2-butanone was purged with nitrogen for 30 min, the reaction vessel was heated to 80° C. with stirring, and the monomer solution prepared as described above was added dropwise thereto over 3 hrs using a dropping funnel. A time point at which the dropwise addition was started was defined as a polymerization starting time, and the polymerization reaction was performed for 6 hrs.

After the completion of the polymerization, the polymerization solution was cooled to no higher than 30° C. by water-cooling, and charged into 600 g of a solution containing methanol and water at a ratio of 8:2 to precipitate the resin. After removing the supernatant solution, 120 g of methanol was added to the precipitated resin to wash the resin. The supernatant liquid was removed, and thereafter the resin was dried at 50° C. for 17 hrs to obtain a polymer (C-3) of the compounds (M-4), and (M-12) (weight: 20 g; yield: 67%). The polymer had an Mw of 5,900, Mw/Mn of 1.4, and the content of fluorine atoms of 9.5% by mass.

Preparation of Composition for an Upper Layer Film

Synthesis Example 7

Preparation of Polymer for an Upper Layer Film (1)

A monomer solution (i) was prepared beforehand by dissolving 22.26 g of the compound (M-10) and 4.64 g of 2,2-azobis(2-methylisomethylpropionate) in 25 g of methylethyl ketone, and a monomer solution (ii) was prepared beforehand by dissolving 27.74 g of the compound (M-14) in 25 g of methylethyl ketone. On the other hand, a 500 mL three-neck flask equipped with a thermometer and a dropping funnel which had been charged with 100 g of methylethyl ketone was purged with nitrogen for 30 min. After the nitrogen-purge, the interior of the flask was heated while stirring with a magnetic stirrer such that the temperature rise to 80° C.

The monomer solution (i) which had been prepared beforehand was added dropwise using a dropping funnel over 20 min, and aged for 20 min. Thereafter, the monomer solution (ii) was subsequently added dropwise over 20 min. Thereafter, the reaction was permitted for additional 1 hour, and the mixture was cooled to no higher than 30° C. to give a copolymerization liquid. The resulting copolymerization liquid was concentrated to 150 g, and then transferred into a separatory funnel. To this separatory funnel were charged 50 g of methanol and 400 g of n-hexane to perform purification by separation. Following the separation, the underlayer liquid was recovered. The underlayer liquid recovered was replaced with 4-methyl-2-pentanol to give a resin solution. The polymer contained in the resulting resin solution had Mw of 5,730 and Mw/Mn of 1.23, with the yield being 26% by mass. Also, the content of each of the structural units derived from the compound (M-10) and the compound (M-14) was 50.3:49.7, and the content of fluorine atoms was 43.6% by mass. The polymer was designated as polymer for an upper layer film (1).

Synthesis Example 8

Preparation of Polymer for an Upper Layer Film (2)

A monomer solution containing 46.95 g (85% by mole) of the compound (M-14), and 6.91 g of 2,2'-azobis-(methyl 2-methylpropionate) dissolved in 100 g of isopropyl alcohol was prepared. On the other hand, a 500 mL three-necked flask equipped with a thermometer and a dropping funnel was charged with 50 g of isopropyl alcohol, and purged with nitrogen for 30 min. After the nitrogen purge, the interior of the flask was heated to 80° C. while stirring with a magnetic stirrer. The monomer solution which had been prepared beforehand was added dropwise using a dropping funnel over 2 hrs.

After the completion of the dropwise addition, the reaction was allowed for additional 1 hour, and thereto was added 10 g of a solution of 3.05 g (15% by mole) of the compound (S-5) in isopropyl alcohol over 30 min, followed by allowing for the reaction for additional 1 hour. The mixture was cooled to no higher than 30° C. to give a polymerization reaction solution. After the resulting polymerization reaction solution was concentrated to 150 g, it was transferred to a separatory funnel. This separatory funnel was charged with 50 g of methanol and 600 g of n-hexane, and separation purification was performed. After the separation, the underlayer liquid was recovered. The underlayer liquid thus recovered was diluted with isopropyl alcohol to 100 g, and again transferred to a separatory funnel. The separatory funnel was charged with 50 g of methanol and 600 g of n-hexane, and separation purification was performed. After the separation, the underlayer liquid was recovered. The underlayer liquid thus recovered was replaced with 4-methyl-2-pentanol, thereby adjusting the total amount to 250 g. After the adjustment, 250 g of water was added thereto, and separation purification was performed. After the separation, the upper layer liquid was recovered.

The upper layer liquid thus recovered was replaced with 4-methyl-2-pentanol to give a resin solution. The polymer contained in the resulting resin solution had Mw of 9,760, and Mw/Mn of 1.51, with the yield being 65% by mass. Also, the content (% by mole) of each of the structural units derived from the compound (M-14) and the compound (M-15) was 95:5, and the content of fluorine atoms was 36.8% by mass. This polymer was designated as polymer for an upper layer film (2).

Preparation of Composition for Forming Upper Layer Film (G)

A composition for forming an upper layer film (G) was prepared by mixing 7 parts by mass of the polymer for an upper layer film (1) prepared in Synthesis Example 7, 93 parts of the polymer for an upper layer film (2) prepared in Synthesis Example 8, 10 parts by mass of diethylene glycol monoethyl ether acetate, 10 parts by mass of 4-methyl-2-hexanol (hereinafter, may be also referred to as "MIBC"), and 90 parts by mass of diisoamyl ether (hereinafter, may be also referred to as "DIAE").

Preparation of Radiation-Sensitive Resin Composition

Example 6

A radiation-sensitive resin composition was prepared by blending 100 parts by mass of (B-1) as the polymer (B), 8.1 parts by mass of (A-1) as the compound (A), 0.9 parts by mass of (D-1) as the nitrogen-containing compound (D) and 30 parts by mass of γ-butyrolactone (F-1) as the uneven distribution accelerator (F), further mixing therewith 1,250 parts by mass of propylene glycol monomethyl ether acetate (E-1) and 520 parts by mass of cyclohexanone (E-2) as the solvent (E), and then filtering through a filter.

Examples 7 to 23 and Comparative Examples 1 to 13

Radiation-sensitive resin compositions were prepared in a similar manner to Example 6 except that each component of the type and the amount shown in Tables 1-1 and 1-2, and Tables 2-1 and 2-2 was used. It is to be noted that in Tables 1-1 and 1-2, "-" indicates that no corresponding component was used.

Details of each component used in Examples and Comparative Examples are shown below.
(D) Nitrogen-Containing Compound
D-1: 4-hydroxy-N-t-amyloxycarbonylpiperidine

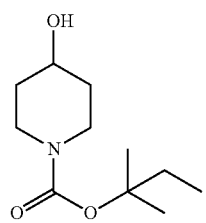

(D-1)

D-2: 2,6-diisopropylaniline

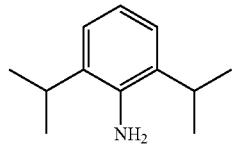

(D-2)

D-3: 2-phenylbenzimidazole

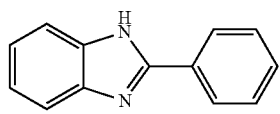

(D-3)

D-4: triphenylsulfonium salicylate

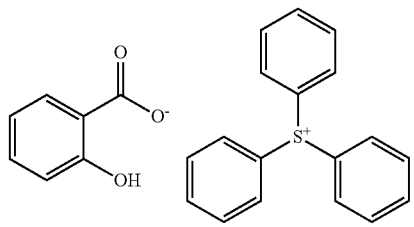

(D-4)

D-5: triphenylsulfonium camphorsulfonate

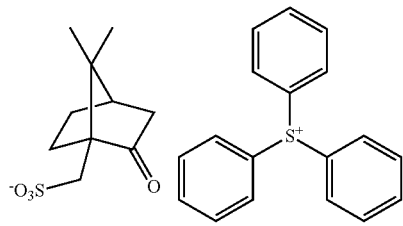

(D-5)

Pattern-Forming Method
Pattern-Forming Method (P-1)

An underlayer antireflection film having a film thickness of 77 nm was formed on the surface of an 8-inch silicon wafer using an agent for forming underlayer antireflective coating (trade name "ARC29A", manufactured by Nissan Chemical Industries, Ltd.). On the surface of this substrate was applied the radiation-sensitive resin composition by spin coating, and SB (Soft Baking) was carried out on a hot plate at 120° C. for 60 sec to form a photoresist film having a film thickness of 120 nm.

This photoresist film was exposed through a mask pattern using a full field stepper (trade name "NSRS306C", manufactured by Nikon Corporation). Thereafter, PEB was carried out at 90° C. for 60 sec, and then the film was developed with a 2.38% aqueous tetramethylammonium hydroxide solution (hereinafter, also referred to as "aqueous TMAH solution") at 25° C. for 30 sec, washed with water and dried to form a positive type resist pattern. In accordance with this method, an exposure dose at which a line-and-space of 1:1 with a line width of 90 nm was formed through a mask for pattern formation with a line of 90 nm and a pitch of 180 nm is defined as "optimum exposure dose". It is to be noted that a scanning electron microscope (S-9380, Hitachi High-Technologies Corporation) was used for the measurement of the lengths. This pattern-forming method was designated as (P-1).

Pattern-Forming Method (P-2)

A photoresist film having a film thickness of 75 nm was formed using the radiation-sensitive resin composition on a 12-inch silicon wafer having an underlayer antireflection film which had been formed similarly to Pattern-Forming Method (P-1), and soft baking (SB) was carried out at 120° C. for 60 sec. Next, the composition for forming an upper layer film (G) was spin coated on the photoresist film thus formed, and subjected to PB (90° C., for 60 sec) to form a an upper layer film having a film thickness of 90 nm. Thereafter, exposure was carried out through a mask pattern using an ArF excimer laser immersion scanner (trade name "NSR S610C", manufactured by Nikon Corporation) under conditions involving NA of 1.3, a ratio of 0.800, and setting of "annular". After the exposure, post baking (PEB) was carried out at 90° C. for 60 sec. Thereafter, development with a 2.38% aqueous TMAH solution, followed by washing with water and drying resulted in formation of a positive type resist pattern. In accordance with this method, an exposure dose at which a line-and-space of 1:1 with a line width of 50 nm was formed through a mask for pattern formation with a line of 50 nm and a pitch of 100 nm is defined as "optimum exposure dose". It is to be noted that a scanning electron microscope (CG-4000, Hitachi High-Technologies Corporation) was used for the measurement of the lengths. This pattern-forming method was designated as (P-2).

Pattern-Forming Method (P-3)

A photoresist film having a film thickness of 75 nm was formed using the radiation-sensitive resin composition on a 12-inch silicon wafer having an underlayer antireflection film which had been formed similarly to Pattern-Forming Method (P-1), and soft baking (SB) was carried out at 120° C. for 60 sec. Next, this photoresist film was subjected to exposure through a mask pattern using the ArF excimer laser immersion scanner under conditions involving NA of 1.3, a ratio of 0.800, and setting of "annular". After the exposure, post baking (PEB) was carried out at 90° C. for 60 sec. Thereafter, development with a 2.38% aqueous TMAH solution, followed by washing with water and drying resulted in formation of a positive type resist pattern. In accordance with this method, an exposure dose at which a line-and-space of 1:1 with a line width of 50 nm was formed through a mask with a line of 50 nm and a pitch of 100 nm is defined as "optimum exposure dose". It is to be noted that a scanning electron microscope (CG-4000, Hitachi High-Technologies Corporation) was used for the measurement of the lengths. This pattern-forming method was designated as (P-3).

Evaluation of MEEF

LS patterns were formed at the aforementioned optimum exposure dose through mask patterns for pattern formation with a line of 86 nm and a pitch of 180 nm, a line of 88 nm and a pitch of 180 nm, a line of 90 nm and a pitch of 180 nm, a line of 92 nm and a pitch of 180 nm, and a line of 94 nm and a pitch of 180 nm, respectively, in the case in which the pattern-forming method (P-1) was employed, whereas LS patterns were formed at the aforementioned optimum exposure dose through mask patterns for pattern formation with a line of 48 nm and a pitch of 100 nm, a line of 49 nm and a pitch of 100 nm, a line of 50 nm and a pitch of 100 nm, a line of 51 nm and a pitch of 100 nm, and a line of 52 nm and a pitch of 100 nm, respectively, in the case in which the pattern-forming method (P-2) or (P-3) was employed pattern-forming method. In this process, the line width (nm) formed on the resist film with each mask pattern (ordinate) was plotted against the line size (nm) of the mask (abscissa) to obtain a straight line, and a slope of the straight line was calculated as MEEF. With respect to the MEEF (the slope of the straight line), the value of more approximate to 1 indicates favorable mask reproducibility. The results are together shown in Tables 1-1 and 1-2, and Tables 2-1 and 2-2.

TABLE 1-1

| | (A) Component | | (B) Polymer | | (C) Polymer | | (D) Nitrogen-containing compound | | (E) Solvent | | (F) Uneven distribution accelerator | | Pattern-forming method | MEEF |
|---|---|---|---|---|---|---|---|---|---|---|---|---|---|---|
| | type | parts by mass | type | parts by mass | type | parts by mass | type | parts by mass | type | parts by mass | type | parts by mass | | |
| Example 6 | A-1 | 8.1 | B-1 | 100 | — | | D-1 | 0.9 | E-1 | 1,250 | F-1 | 30 | P-1 | 3.6 |
| | | | | | | | | | E-2 | 520 | | | | |
| Example 7 | A-1 | 11.3 | B-1 | 100 | — | | D-1 | 1.5 | E-1 | 2,500 | F-1 | 30 | P-2 | 3.2 |
| | | | | | | | | | E-2 | 1,100 | | | | |
| Example 8 | A-1 | 11.3 | B-1 | 100 | — | | D-2 | 1.3 | E-1 | 2,500 | — | | P-2 | 3.3 |
| | | | | | | | | | E-2 | 1,100 | | | | |
| Example 9 | A-1 | 11.3 | B-1 | 100 | — | | D-3 | 1.1 | E-1 | 2,500 | F-1 | 30 | P-2 | 3.6 |
| | | | | | | | | | E-2 | 1,100 | | | | |
| Example 10 | A-1 | 11.3 | B-1 | 100 | — | | D-4 | 7.1 | E-1 | 2,500 | F-1 | 50 | P-2 | 2.9 |
| | | | | | | | | | E-2 | 1,100 | | | | |
| Example 11 | A-1 | 11.3 | B-1 | 100 | — | | D-5 | 6.2 | E-1 | 2,500 | — | | P-2 | 3.3 |
| | | | | | | | | | E-2 | 1,100 | | | | |
| Example 12 | A-1 | 11.3 | B-1 | 100 | C-1 | 5 | D-1 | 1.5 | E-1 | 2,500 | F-1 | 30 | P-3 | 3.2 |
| | | | | | | | | | E-2 | 1,100 | | | | |
| Example 13 | A-1 | 11.3 | B-1 | 100 | C-2 | 5 | D-2 | 1.3 | E-1 | 2,500 | F-1 | 50 | P-3 | 3.5 |
| | | | | | | | | | E-2 | 1,100 | | | | |
| Example 14 | A-1 | 11.3 | B-1 | 100 | C-1 | 2 | D-5 | 7.7 | E-1 | 2,500 | F-1 | 50 | P-3 | 3.1 |
| | | | | | C-3 | 3 | | | E-2 | 1,100 | | | | |

TABLE 1-2

| | (A) Component | | (B) Polymer | | (C) Polymer | | (D) Nitrogen-containing compound | | (E) Solvent | | (F) Uneven distribution accelerator | | Pattern-forming method | MEEF |
|---|---|---|---|---|---|---|---|---|---|---|---|---|---|---|
| | type | parts by mass | type | parts by mass | type | parts by mass | type | parts by mass | type | parts by mass | type | parts by mass | | |
| Example 15 | A-1 | 11.3 | B-2 | 100 | C-3 | 5 | D-4 | 7.1 | E-1 E-2 | 2,500 1,100 | F-1 | 200 | P-3 | 3.2 |
| Example 16 | A-1 | 11.3 | B-3 | 100 | C-2 | 3 | D-4 | 7.1 | E-1 E-2 | 2,500 1,100 | F-1 | 200 | P-3 | 3 |
| Example 17 | A-1 | 11.3 | B-1 B-2 | 50 50 | C-2 | 3 | D-4 | 7.1 | E-1 E-2 | 2,500 1,100 | F-1 | 200 | P-3 | 3.2 |
| Example 18 | A-1 | 11.3 | B-1 | 100 | C-3 | 5 | D-4 | 7.1 | E-1 E-2 | 2,500 1,100 | F-1 | 100 | P-3 | 3 |
| Example 19 | A-2 | 12.3 | B-1 | 100 | C-3 | 5 | D-4 | 7.1 | E-1 E-2 | 2,500 1,100 | F-1 | 100 | P-3 | 2.8 |
| Example 20 | A-3 | 15.7 | B-1 | 100 | C-3 | 5 | D-4 | 7.1 | E-1 E-2 | 2,500 1,100 | F-1 | 100 | P-3 | 2.7 |
| Example 21 | A-4 | 13.7 | B-1 | 100 | C-3 | 5 | D-4 | 7.1 | E-1 E-2 | 2,500 1,100 | F-1 | 100 | P-3 | 3 |
| Example 22 | A-1 A-3 | 5.6 7.9 | B-1 | 100 | C-3 | 5 | D-4 | 7.1 | E-1 E-2 | 2,500 1,100 | F-1 | 200 | P-3 | 2.9 |
| Example 23 | A-1 A-4 | 5.6 6.9 | B-1 | 100 | C-3 | 5 | D-4 | 7.1 | E-1 E-2 | 2,500 1,100 | F-1 | 200 | P-3 | 3.1 |

TABLE 2-1

| | (A) Component | | (B) Polymer | | (C) Polymer | | (D) Nitrogen-containing compound | | (E) Solvent | | (F) Uneven distribution accelerator | | Pattern-forming method | MEEF |
|---|---|---|---|---|---|---|---|---|---|---|---|---|---|---|
| | type | parts by mass | type | parts by mass | type | parts by mass | type | parts by mass | type | parts by mass | type | parts by mass | | |
| Comparative Example 1 | A'-2 | 8.1 | B-1 | 100 | — | | D-1 | 0.9 | E-1 E-2 | 1,250 520 | F-1 | 30 | P-1 | 3.9 |
| Comparative Example 2 | A'-2 | 11.4 | B-1 | 100 | — | | D-1 | 1.5 | E-1 E-2 | 2,500 1,100 | F-1 | 30 | P-2 | 4 |
| Comparative Example 3 | A'-2 | 11.4 | B-1 | 100 | — | | D-2 | 1.3 | E-1 E-2 | 2,500 1,100 | — | | P-2 | 4 |
| Comparative Example 4 | A'-2 | 11.4 | B-1 | 100 | — | | D-3 | 1.1 | E-1 E-2 | 2,500 1,100 | F-1 | 30 | P-2 | 3.7 |
| Comparative Example 5 | A'-2 | 11.4 | B-1 | 100 | — | | D-4 | 7.1 | E-1 E-2 | 2,500 1,100 | F-1 | 50 | P-2 | 3.9 |
| Comparative Example 6 | A'-2 | 11.4 | B-1 | 100 | — | | D-5 | 6.2 | E-1 E-2 | 2,500 1,100 | — | | P-2 | 3.8 |
| Comparative Example 7 | A'-2 | 11.4 | B-1 | 100 | C-1 | 5 | D-1 | 1.5 | E-1 E-2 | 2,500 1,100 | F-1 | 30 | P-3 | 4.2 |
| Comparative Example 8 | A'-2 | 11.4 | B-1 | 100 | C-2 | 5 | D-2 | 1.3 | E-1 E-2 | 2,500 1,100 | F-1 | 50 | P-3 | 4 |
| Comparative Example 9 | A'-2 | 11.4 | B-1 | 100 | C-1 C-3 | 2 3 | D-5 | 7.7 | E-1 E-2 | 2,500 1,100 | F-1 | 50 | P-3 | 3.4 |

TABLE 2-2

| | (A) Component | | (B) Polymer | | (C) Polymer | | (D) Nitrogen-containing compound | | (E) Solvent | | (F) Uneven distribution accelerator | | Pattern-forming method | MEEF |
|---|---|---|---|---|---|---|---|---|---|---|---|---|---|---|
| | type | parts by mass | type | parts by mass | type | parts by mass | type | parts by mass | type | parts by mass | type | parts by mass | | |
| Comparative Example 10 | A'-1 | 10.1 | B-2 | 100 | C-3 | 5 | D-4 | 7.1 | E-1 E-2 | 2,500 1,100 | F-1 | 200 | P-3 | 4.2 |
| Comparative Example 11 | A'-1 | 10.1 | B-3 | 100 | C-2 | 3 | D-4 | 7.1 | E-1 E-2 | 2,500 1,100 | F-1 | 200 | P-3 | 4.4 |
| Comparative Example 12 | A'-1 | 10.1 | B-1 B-2 | 50 50 | C-2 | 3 | D-4 | 7.1 | E-1 E-2 | 2,500 1,100 | F-1 | 200 | P-3 | 4 |
| Comparative Example 13 | A'-2 | 11.4 | B-1 | 100 | C-3 | 5 | D-4 | 7.1 | E-1 E-2 | 2,500 1,100 | F-1 | 100 | P-3 | 3.5 |

With regard to Examples shown in Tables 1-1 and 1-2, and Comparative Examples shown in Tables 2-1 and 2-2, Example 6 is relevant to Comparative Example 1 but the acid generating component is different. Similarly, Examples 7 to 23 can be also found to be relevant to Comparative Examples, with an attention to the difference in the component (A), i.e., the acid generating component. When each Example is compared with relevant each Comparative Example, it was revealed that the resist pattern formed using the radiation-sensitive resin composition enabled the MEEF to be reduced.

According to the embodiment of the present invention, a radiation-sensitive resin composition that satisfies basic characteristics such as sensitivity and resolving ability, as well as MEEF performances enough, and a compound that can be suitably used as a material of the composition can be provided. Therefore, the compound, and the radiation-sensitive resin composition containing the compound may be suitably used in lithography steps of semiconductor devices and the like for which miniaturization advances in recent years.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:
a compound represented by formula (1); and
a polymer that comprises a structural unit comprising an acid-labile group:

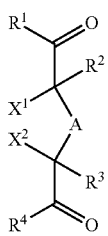

(1)

wherein, in the formula (1),
$R^1$ represents —$ZR^5$, and $R^4$ represents —$ZR^6$, wherein each Z represents —O— or —NH—, and $R^5$ and $R^6$ each independently represent an alicyclic group having 3 to 10 carbon atoms or a group comprising a lactone structure having 4 to 12 carbon atoms;
$R^2$ and $R^3$ each independently represent a hydrogen atom or a monovalent organic group;
$X^1$ and $X^2$ each independently represent a hydrogen atom, a hydroxyl group, a thiol group, a sulfonyl group or a monovalent organic group, or $X^1$ and $X^2$ taken together represent —S—, —O—, —$SO_2$—, an alkanediyl group having 1 to 10 carbon atoms or a combined group thereof; and
A represents an ethanediyl group,
wherein at least one hydrogen atom included in $X^1$, $X^2$ and A is substituted by —Y—$SO_3^-M^+$, wherein Y represents an alkanediyl group having 1 to 10 carbon atoms that is substituted with a fluorine atom, and two fluorine atoms bond to a carbon atom adjacent to $SO_3^-$, and $M^+$ represents a monovalent onium cation, and in the case where —Y—$SO_3^-M^+$ is present in a plurality of number, a plurality of Ys are each identical or different and a plurality of $M^+$s are each identical or different.

2. The radiation-sensitive resin composition according to claim 1, wherein the compound is represented by formula (2):

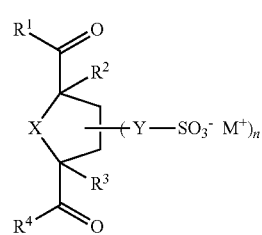

(2)

wherein, in the formula (2), $R^1$ to $R^4$, Y and $M^+$ are as defined in the formula (1); X represents —S—, —O—, —$SO_2$—, an alkanediyl group having 1 to 10 carbon atoms or a combined group thereof; and n is an integer of 1 to 4.

3. The radiation-sensitive resin composition according to claim 1, wherein
$R^1$ represents —$OR^5$, and $R^4$ represents —$OR^6$, wherein $R^5$ and $R^6$ each independently represent an alicyclic group having 3 to 10 carbon atoms or a group comprising a lactone structure having 4 to 12 carbon atoms.

4. The radiation-sensitive resin composition according to claim 1, wherein the polymer further comprises a structural unit comprising a lactone structure or a cyclic carbonate structure, a structural unit comprising a polar group, or a combination thereof.

5. The radiation-sensitive resin composition according to claim 1, wherein $M^+$ is a sulfonium cation or an iodonium cation.

6. The radiation-sensitive resin composition according to claim 1, further comprising a fluorine atom-containing polymer.

7. The radiation-sensitive resin composition according to claim 1, further comprising a nitrogen-containing compound.

8. A compound represented by formula (1):

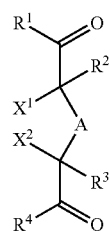

(1)

wherein, in the formula (1),
$R^1$ represents —$ZR^5$, and $R^4$ represents —$ZR^6$, wherein each Z represents —O— or —NH—, and $R^5$ and $R^6$ each independently represent an alicyclic group having 3 to 10 carbon atoms or a group comprising a lactone structure having 4 to 12 carbon atoms;
$R^2$ and $R^3$ each independently represent a hydrogen atom or a monovalent organic group;
$X^1$ and $X^2$ each independently represent a hydrogen atom, a hydroxyl group, a thiol group, a sulfonyl group or a monovalent organic group, or $X^1$ and $X^2$ taken together represent —S—, —O—, —$SO_2$—, an alkanediyl group having 1 to 10 carbon atoms or a combined group thereof; and A represents an ethanediyl group, wherein at least one hydrogen atom included in $X^1$, $X^2$ and A is substituted by —Y—$SO_3^-M^+$, wherein Y represents an alkanediyl group having 1 to 10 carbon atoms that is substituted with a fluorine atom and two fluorine atoms bond to a carbon atom adjacent to $SO_3^-$, and $M^+$ represents a monovalent onium cation, and in the case where —Y—$SO_3^-M^+$ is present in a plurality of number, a plurality of Ys are each identical or different and a plurality of $M^+$s are each identical or different.

9. The compound according to claim 8, wherein $R^1$ represents —$OR^5$, and $R^4$ represents —$OR^6$, wherein $R^5$ and $R^6$ each independently represent an alicyclic group having 3 to 10 carbon atoms or a group comprising a lactone structure having 4 to 12 carbon atoms.

10. A compound represented by formula (2):

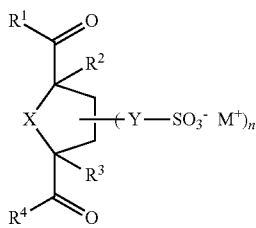

(2)

wherein, in the formula (2), $R^1$ represents —$ZR^5$, and $R^4$ represents —$ZR^6$, wherein each Z represents —O— or —NH—, and $R^5$ and $R^6$ each independently represent an alicyclic group having 3 to 10 carbon atoms or a group comprising a lactone structure having 4 to 12 carbon atoms;

$R^2$ and $R^3$ each independently represent a hydrogen atom or a monovalent organic group;

Y represents an alkanediyl group having 1 to 10 carbon atoms that is substituted with a fluorine atom, and two fluorine atoms bond to a carbon atom adjacent to $SO_3^-$;

$M^+$ represents a monovalent onium cation;

X represents —S—, —O—, —$SO_2$—, an alkanediyl group having 1 to 10 carbon atoms or a combined group thereof;

n is an integer of 1 to 4; and in the case where —Y—$SO_3^-M^+$ is present in a plurality of number, a plurality of Ys are each identical or different and a plurality of $M^+$s are each identical or different.

11. The compound according to claim 10, wherein $R^1$ represents —$OR^5$, and $R^4$ represents —$OR^6$, wherein $R^5$ and $R^6$ each independently represent an alicyclic group having 3 to 10 carbon atoms or a group comprising a lactone structure having 4 to 12 carbon atoms.

* * * * *